(12) United States Patent
Edmundson et al.

(10) Patent No.: US 11,212,916 B2
(45) Date of Patent: Dec. 28, 2021

(54) FLEXIBLE PRINTED CIRCUITS FOR DERMAL APPLICATIONS

(71) Applicant: W.L. Gore & Associates, Inc., Newark, DE (US)

(72) Inventors: Mark D. Edmundson, Philadelphia, PA (US); Paul D. Gassler, Lincoln University, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 17/050,466

(22) PCT Filed: May 8, 2018

(86) PCT No.: PCT/US2018/031546
§ 371 (c)(1),
(2) Date: Oct. 26, 2020

(87) PCT Pub. No.: WO2019/216883
PCT Pub. Date: Nov. 14, 2019

(65) Prior Publication Data
US 2021/0112657 A1    Apr. 15, 2021

(51) Int. Cl.
*H05K 1/00* (2006.01)
*H05K 1/03* (2006.01)
(Continued)

(52) U.S. Cl.
CPC ........... *H05K 1/0393* (2013.01); *H05K 1/028* (2013.01); *H05K 1/0313* (2013.01); *H05K 1/189* (2013.01);
(Continued)

(58) Field of Classification Search
CPC .... H05K 1/0393; H05K 1/028; H05K 1/0313; H05K 1/189; H05K 2201/015; A61B 2562/166
(Continued)

(56) References Cited

U.S. PATENT DOCUMENTS 3,953,566 A    4/1976 Gore
4,443,511 A    4/1984 Worden et al.
(Continued)

FOREIGN PATENT DOCUMENTS

CA    2900130 A1    10/2015
EP    0317256 A2    5/1989
(Continued)

OTHER PUBLICATIONS

Hong et al., "OmniDirectionally Stretchable and Transparent Graphene Electrodes," ACS Nano (2016); 10:9446-9455.
(Continued)

*Primary Examiner* — Binh B Tran
(74) *Attorney, Agent, or Firm* — Greenberg Traurig, LLP

(57) ABSTRACT

The present invention is directed to flexible printed circuits for dermal applications that include a synthetic polymer membrane 702 and at least one electrically conductive trace 705. In an alternative embodiment, the electrically conductive trace is located on both sides of the microporous synthetic polymer membrane. The electrically conductive trace may be located on the surface of or be imbibed into the pores and through the thickness of a microporous synthetic polymer membrane. The flexible printed circuits may be electrically coupled to an electronic component to form a flexible printed circuit board and adhered to the skin 701 by a dermally acceptable adhesive. The flexible printed circuit or the flexible printed circuit board may be coupled to an electronic module 703 to form a hybrid flexible printed
(Continued)

circuit board. The flexible printed circuit, flexible printed circuit board, and hybrid flexible printed circuit board achieve a balance of comfort, flexibility, and durability for on-skin use.

45 Claims, 17 Drawing Sheets

(51) Int. Cl.
  H05K 1/02 (2006.01)
  H05K 1/18 (2006.01)
(52) U.S. Cl.
  CPC .. A61B 2562/166 (2013.01); H05K 2201/015 (2013.01)
(58) Field of Classification Search
  USPC ....................................................... 361/750
  See application file for complete search history.

(56) References Cited

U.S. PATENT DOCUMENTS

| | | | |
|---|---|---|---|
| 4,557,957 A | 12/1985 | Manniso | |
| 4,720,400 A | 1/1988 | Manniso | |
| 4,972,846 A | 11/1990 | Owens et al. | |
| 4,985,296 A | 1/1991 | Mortimer | |
| 5,026,513 A | 6/1991 | House et al. | |
| 5,148,806 A | 9/1992 | Fukui et al. | |
| 5,183,545 A | 2/1993 | Branca et al. | |
| 5,188,890 A | 2/1993 | Ohashi et al. | |
| 5,269,810 A | 12/1993 | Hull et al. | |
| 5,476,589 A | 12/1995 | Bacino | |
| 5,524,908 A | 6/1996 | Reis | |
| 5,527,569 A | 6/1996 | Hobson et al. | |
| 5,753,358 A * | 5/1998 | Korleski | H05K 1/0353 428/308.4 |
| 5,785,787 A | 7/1998 | Wojnarowski et al. | |
| 5,885,738 A | 3/1999 | Hannon | |
| 5,904,978 A | 5/1999 | Hanrahan et al. | |
| 5,910,354 A | 6/1999 | Meola et al. | |
| 6,016,848 A | 1/2000 | Egres | |
| 6,210,789 B1 | 4/2001 | Hanrahan | |
| 6,218,000 B1 | 4/2001 | Rudolf et al. | |
| 6,379,745 B1 | 4/2002 | Kydd et al. | |
| 6,528,572 B1 | 3/2003 | Patel et al. | |
| 6,689,835 B2 | 2/2004 | Amarasekera et al. | |
| 6,737,158 B1 | 5/2004 | Thompson | |
| 7,306,729 B2 | 12/2007 | Bacino et al. | |
| 7,354,988 B2 | 4/2008 | Charati et al. | |
| 7,481,952 B2 | 1/2009 | Ren et al. | |
| 7,678,701 B2 | 3/2010 | Tredwell et al. | |
| 7,789,908 B2 | 9/2010 | Sowinski et al. | |
| 7,932,184 B2 | 4/2011 | Ishii | |
| 8,278,757 B2 | 10/2012 | Crain et al. | |
| 8,974,739 B2 | 3/2015 | Yoshida | |
| 9,288,903 B2 | 3/2016 | Hasegawa et al. | |
| 9,441,088 B2 | 9/2016 | Sbriglia et al. | |
| 9,446,232 B2 | 9/2016 | Duncan et al. | |
| 9,573,339 B2 | 2/2017 | Hodgins et al. | |
| 9,926,416 B2 | 3/2018 | Sbriglia | |
| 9,932,429 B2 | 4/2018 | Sbriglia | |
| 2003/0181568 A1 | 9/2003 | Amarasekera et al. | |
| 2004/0059717 A1 | 3/2004 | Klare et al. | |
| 2004/0173978 A1 | 9/2004 | Bowen et al. | |
| 2009/0008142 A1 | 1/2009 | Shimizu | |
| 2009/0227165 A1 | 9/2009 | Imai | |
| 2011/0167547 A1 | 7/2011 | Jain | |
| 2013/0160183 A1 | 7/2013 | White | |
| 2014/0121557 A1 | 5/2014 | Gannon et al. | |
| 2014/0242355 A1 | 8/2014 | Castille | |
| 2016/0032069 A1 | 2/2016 | Sbriglia | |
| 2016/0167291 A1 | 6/2016 | Zagl | |
| 2016/0358849 A1 | 12/2016 | Jur | |
| 2018/0067529 A1 | 3/2018 | Jhong | |
| 2019/0290496 A1 * | 9/2019 | Brownhill | A61F 13/00068 |
| 2020/0221580 A1 * | 7/2020 | Tavakoli | B41M 3/006 |

FOREIGN PATENT DOCUMENTS

| | | | |
|---|---|---|---|
| GB | 1409229 A | | 10/1975 |
| WO | 9703812 A1 | | 2/1997 |
| WO | 2004005413 A1 | | 1/2004 |
| WO | 2016135188 A1 | | 9/2016 |
| WO | 2017086583 A1 | | 5/2017 |

OTHER PUBLICATIONS

Hu et al., "Inkjet Printing of Nanoporous Gold Electrode Arrays on Cellulose Membranes for High-Sensitive Paper-Like Electrochemical Oxygen Sensors Using Ionic Liquid Electrolytes," Anal. Chem. (2012); 84:3745-3750.
Jeong et al., "Solderable and Electroplatable flexible electronic circuit on a porous stretchable elastomer," Nat. Commun., DOI: 10.1038/ncomms1980, (2012).
Lim et al., "Surface Treatments for Inkjet Printing onto a PTFE-Based Substrate for High Frequency Applications," Ind. Eng. Chem. Res., (2013); 52:11564-11574.
Merilampi et al., "The characterization of electrically conductive silver ink patterns on flexible substrates," Microelectronics Reliability (2009); 49:782-790.
Paiz et al., "Adhesion of Continuous Ink Jet Inks on PTFE," Wire and Cable Technology International (May/Jun. 2013); 5 pages.
Park et al., "Design of conductive composite elastomers for stretchable electronics," Nano Today (2014); 9:244-260.
Pu et al., "Highly Stretchable Microsupercapacitor Arrays with Honeycomb Structures for Integrated Wearable Electronic Systems," ACS Nano (2016); 10:9306-9315.
Rogers et al., "Materials and Mechanics for Stretchable Electronics," Science (2010); 327:1603-1607.
Vuorinen et al., "Inkjet-Printer Graphene/PEDOT:PSS Temperature Sensors on a Skin Conformable Polyurethane Substrate," Scientific Reports, DOI: 10.1038/srep35289 (Oct. 2016).
Yao et al., "Nanomaterial-Enabled Stretchable Conductors: Strategies, Material and Devices," Adv. Mater., DOI: 10.1002/adma. 201404446 (2015).
Yetisen et al., "Nanotechnology in Textiles," ACS Nano (2016); 10:3042-3068.

* cited by examiner

FLEXIBLE PRINTED CIRCUITS FOR DERMAL APPLICATIONS

FIELD

The present disclosure relates generally to flexible printed circuits, and more specifically, to flexible printed circuits, flexible circuit boards, and hybrid flexible circuit boards that are applied dermally and are comfortable for an extended period of time.

BACKGROUND

Conventionally, flexible circuits are built upon stiff materials such as Mylar or Kapton®. While these materials are considered flexible in comparison to the traditional copper and fiberglass circuit boards, they do not exhibit flexibility that is comparable to that of textiles or skin. The incorporation of flexible circuits into garments and/or other skin-worn devices is limited by this stiffness. Indeed, many existing circuit materials are too stiff to be integrated into textiles and remain durably reliable, particularly upon flexing in use and during washing or other cleaning regimens.

In this regard, a number of conductive inks have been developed that are thin and stretchable. These inks are conventionally printed directly onto textiles and are able to retain the flexibility, stretch, and hand of the textile. However, they suffer from significant durability and electrical connectivity problems. For instance, when a textile is stretched, the textile fiber bundles move significantly relative to each other. The conductive inks are incapable of withstanding the elongation required to bridge the gap between the textile fiber bundles, resulting in breaks and open circuits.

The same stretchable conductive inks have been printed onto urethane films and then heat bonded to stretch textiles. This results in a more durable circuit than printing directly onto textiles, however the resulting laminate has significantly less stretch than the original textile. In other existing art, conductive inks have been sandwiched between insulating inks and then thermally laminated to textiles. However, thin coatings of the insulating inks are unable to effectively support the conductive ink. Increasing the thickness of the insulating ink can improve the durability, but only at great expense of the textile's stretchability.

Despite the advances in flexible electrical circuits, a need still exists for durable and effective flexible electrical circuit systems for a variety of applications ranging from garments to medical diagnostic and treatment devices, as well as many other suitable end use applications.

SUMMARY

One embodiment relates to a flexible printed circuit that includes (1) a microporous synthetic polymer membrane having a node and fibril microstructure and a first and second surface, (2) at least one electrically conductive trace located on the first and/or second surface of the microporous synthetic polymer membrane, and (3) a dermally acceptable adhesive positioned on the first and/or second surface of the microporous synthetic polymer membrane. The microporous synthetic polymer membrane may be an expanded polytetrafluoroethylene membrane. In at least one embodiment, the electrically conductive trace is positioned on the first surface of the synthetic polymer membrane and the dermally acceptable adhesive positioned on the second surface of the synthetic polymer membrane. In some embodiments, the electrically conductive trace may be positioned on the first and second surfaces of the synthetic polymer membrane and the dermally acceptable adhesive is positioned on at least one of the first and second surfaces of the synthetic polymer membrane. In some embodiments, an imbibed electrically conductive trace electrically interconnects the electrically conductive trace on the first surface with the electrically conductive trace on the second surface. An insulative overcoat may be positioned over at least a portion of the electrically conductive trace. The electrically conductive trace may be a particle or nanoparticle of silver, platinum, gold, copper, carbon black, and combinations thereof. In addition, the conductive trace may include a continuous network of conductive particles. The electrically conductive trace may have the form of an electrically conductive pattern or a circuit. The flexible circuit has a flexibility of less than about 1.0 newton as evidenced by the Peak Compression Load Test (Compressive Buckling) test method. Also, the load applied to cause a 2× increase in resistance is greater than about 0.7 newtons when tested according to the Load Required to Double the Resistance test method.

The flexible printed circuit may further include at least one electric component to form a flexible circuit board. The electronic component may include electron resistors, capacitors, light emitting diodes (LEDs), integrated circuits, sensors, power sources, data transmitters, data receivers and combinations thereof.

The flexible circuit or the flexible circuit board may be combined with an electronic module to form a hybrid flexible printed circuit board. In some embodiments, the electronic module may be positioned on the same side of the microporous synthetic polymer membrane as the electrically conductive trace. In another embodiment, the electronic module may be configured to be positioned between the microporous synthetic polymer membrane and the skin of a user.

Another embodiment relates to a flexible printed circuit that includes (1) a microporous synthetic polymer membrane, (2) at least one electrically conductive trace located within the microporous synthetic polymer membrane, and (3) a dermally acceptable adhesive positioned on the synthetic polymer membrane. In some embodiments, the electrically conductive trace fill the pores through the thickness of the microporous synthetic polymer membrane. The microporous synthetic polymer membrane may be an expanded polytetrafluoroethylene membrane. The electrically conductive trace may be a particle or nanoparticle of silver, platinum, gold, copper, carbon black, and combinations thereof. In addition, the conductive trace may include a continuous network of conductive particles. The electrically conductive trace may have the form of an electrically conductive pattern or a circuit. The flexible circuit has a flexibility of less than about 1.0 newton as evidenced by the Peak Compression Load Test (Compressive Buckling) test method. Also, the load applied to cause a 2× increase in resistance is greater than about 0.7 newtons when tested according to the Load Required to Double the Resistance test method.

The flexible printed circuits may further include at least one electric component to form a flexible circuit boards. The electronic component may include electron resistors, capacitors, light emitting diodes (LEDs), integrated circuits, sensors, power sources, data transmitters, data receivers and combinations thereof.

The flexible circuit or the flexible circuit board may be combined with an electronic module to form a hybrid flexible printed circuit board. In some embodiments, the electronic module may be positioned on the same side of the microporous synthetic polymer membrane as the electrically conductive trace. In another embodiment, the electronic module may be configured to be positioned between the microporous synthetic polymer membrane and the skin of a user.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
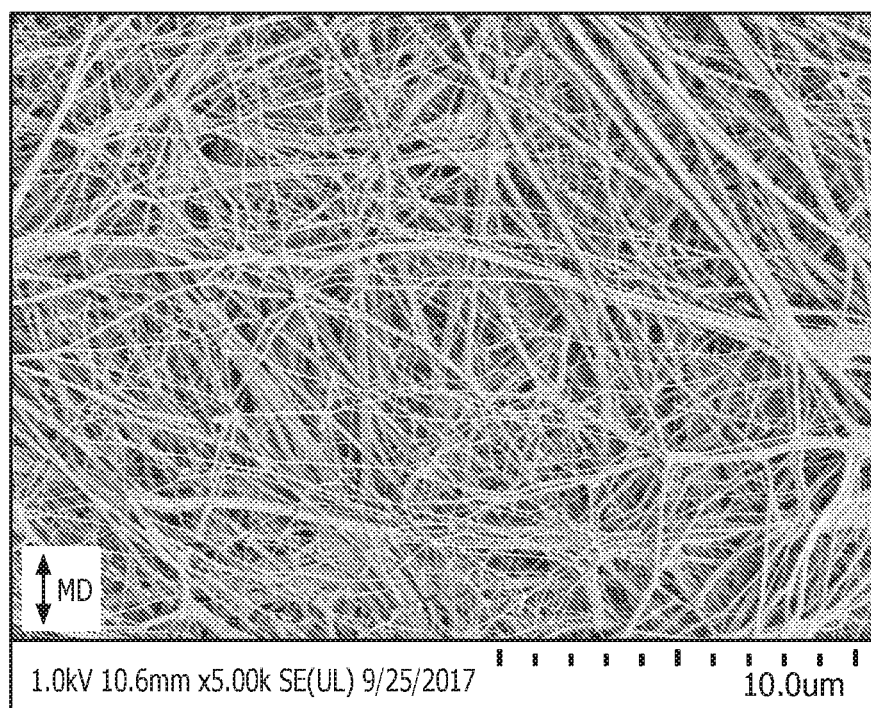
FIG. 1 is a scanning electron micrograph (SEM) image of a microporous expanded polytetrafluoroethylene (ePTFE) membrane (Membrane 1) according to at least one embodiment.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting. It is to be appreciated that the terms "electrically conductive trace", "conductive trace", and "trace" may be used interchangeably herein. The terms "membrane" and "film" may be used interchangeably herein. As used herein, the terms "synthetic polymer membrane" and "microporous synthetic polymer membrane" may be interchangeably used herein.

The present invention is directed to flexible printed circuits for dermal applications that include a microporous synthetic polymer membrane and at least one electrically conductive trace. The electrically conductive trace may be imbibed or otherwise incorporated into the pores and through the thickness of a microporous synthetic polymer membrane to form a flexible printed circuit. In other embodiments, the electrically conductive trace may be positioned on the surface of the microporous synthetic polymer membrane to form a flexible printed circuit. The flexible printed circuits may be electrically coupled and/or adhered to an electronic module and adhered to the skin, such as to the skin of a human, by a dermally acceptable adhesive. The adhesion may be by the application of a discontinuous or continuous adhesive. Additionally, the flexible printed circuit may have electrically coupled thereto an electronic component to create a flexible printed circuit board. An electronic module (e.g., a traditional circuit board) may be coupled to the flexible printed circuit or flexible printed circuit board to create a hybrid flexible printed circuit board.

As discussed above, the flexible printed circuits include at least one electrically conductive trace and a synthetic polymer membrane. The term "electrically conductive trace" as used herein is meant to describe a continuous line or continuous pathway that is able to conduct electrons therethrough. In exemplary embodiments, non-conducting regions are located alongside the electrically conductive trace on or within the synthetic polymer membrane. In some embodiments, an electrically conductive ink may be used to deposit the electrically conductive trace on or into the synthetic polymer membrane. The term "electrically conductive ink" as used herein refers to materials that incorporate electrically conductive particles in a carrier liquid (e.g. a solvent). In some embodiments, the electrically conductive particles include, silver, gold, copper, or platinum particles. Non-limiting examples of suitable electrically conductive inks include 2108-IPA (Nanogap Inc., Richmond, Calif.), PE872 (DuPont, Wilmington, Del.), CI1036 (Engineered Materials Systems, Inc., Delaware, Ohio), and 125-19FS (Creative Materials, Inc., Ayer, Mass.).

Non-limiting examples of other electrically conductive materials that form the electrically conductive trace include electrically conductive metal particles or nanoparticles (e.g., silver, gold, copper, and platinum), particles or nanoparticles of other electrically conductive materials (e.g., graphite or carbon black), electrically conductive nanotubes, electrically conductive metal flakes, electrically conductive polymers, electrically conductive particles, and combinations thereof. As used herein, the term "nanoparticle" is meant to describe a particle that has a size from 1.0 nm to 100 nm in at least one dimension of the conductive particle.

The electrically conductive trace may be in the form of an electrically conductive pattern that can be used to form a circuit through which an electric current may flow. The pattern may create an open path, such as, for example, the parallel lines exemplified in FIG. 4 or the pattern depicted in FIG. 8. In some embodiments, electronic component(s) (e.g., resistors, capacitors, light emitting diodes (LEDs), integrated circuits, sensors, power sources, data transmitters, and/or data receivers) may be electrically coupled (e.g., adhered) to a flexible printed circuit (e.g., the conductive trace pattern shown in FIG. 10) to create a flexible circuit board that can be dermally positioned. As used herein, the phrases "dermally positioned" or "dermally adhered" are meant to denote the application of the flexible printed circuit or flexible printed circuit board onto the skin of a human or animal. The flexible printed circuit and flexible printed circuit board may be used to transmit information, such as the user's heart rate or oxygen saturation in the blood to the user or the user's doctor, for example.

In at least one embodiment, the synthetic polymer membrane is a microporous synthetic polymer membrane or a microporous fluoropolymer membrane having a node and fibril microstructure where the nodes are interconnected by the fibrils and the pores are the voids or space located between the nodes and fibrils throughout the membrane, such as expanded polytetrafluoroethylene (ePTFE). An exemplary node and fibril microstructure is described in U.S. Pat. No. 3,953,566 to Gore.

The microporous synthetic polymer membranes described herein may be differentiated from other membranes or structures in that they have a specific surface area of greater than about 4.0 $m^2/cm^3$, greater than about 10 $m^2/cm^3$, greater than about 50 $m^2/cm^3$, greater than about 75 $m^2/cm^3$, and up to 100 $m^2/cm^3$. In some embodiments, the specific surface area is from about 4.0 $m^2/cm^3$ and 100 $m^2/cm^3$. Herein, specific surface area is defined on the basis of skeletal volume, not envelope volume. In addition, the majority of the fibrils in the microporous synthetic polymer membrane have a diameter that is less than about 1.0 μm, or from about 0.1 μm to about 1.0 μm, from about 0.3 μm to about 1.0 μm, from about 0.5 μm to about 1.0 μm, or from about 0.7 μm to about 1.0 μm. In at least one exemplary embodiment, the synthetic polymer membrane is an expanded polytetrafluoroethylene (ePTFE) membrane. Expanded polytetrafluoroethylene (ePTFE) membranes prepared in accordance with the methods described in U.S. Pat. No. 3,953,566 to Gore, U.S. Patent Publication No. 2004/0173978 to Bowen et al., U.S. Pat. No. 7,306,729 to Bacino et al., U.S. Pat. No. 5,476,589 to Bacino, or U.S. Pat. No. 5,183,545 to Branca et al. may be used herein. Additionally, the microporous synthetic polymer membranes are thin, having a thickness less than about 100 μm, less than about 75 μm, less than about 50 μm, less than about 35 μm, less than about 25 μm, less than about 20 μm, less than about 10 μm, less than about 5 μm, or less than about 3 μm.

In one embodiment, the conductive trace may be applied to the outer surface of the synthetic polymer membrane to form a flexible printed circuit. In at least one embodiment, a stencil having the desired pattern is applied to the surface of the synthetic polymer membrane. Other forms of creating a pattern on the surface of a microporous synthetic polymer membrane known to those of skill in the art are considered to be within the purview of this disclosure. In exemplary embodiments, the synthetic polymer membrane is flat (i.e., planar) and contains no wrinkles when the electrically conductive material is applied. The electrically conductive material (e.g., an electrically conductive ink) is applied over the stencil such that once the stencil is removed, the electrically conductive material remains on the synthetic polymer membrane in the desired pattern, forming the electrically conductive trace. The electrically conductive material may be applied such that the electrically conductive trace is positioned on at least a portion of the outer surface of the synthetic polymer membrane to form the flexible printed circuit. It is to be appreciated that the term "on" as used herein with respect to the conductive trace is meant to denote that the trace is on the surface of the synthetic polymer membrane (i.e., no electrically conductive material is located in the pores of the synthetic polymer membrane) or that the trace is substantially located on the surface of the synthetic polymer membrane (i.e., a negligible amount of an electrically conductive material may be located in the pores of the synthetic polymer membrane). "On" is also meant to denote that the electrically conductive trace may be positioned directly on the substrate (with no intervening elements) or that intervening elements may be present. Although not wishing to be bound by theory, it is believed that the negligible penetration (e.g., a micron) of the electrically conductive material into the pores of the microporous synthetic polymer membrane results in an improved adhesion of the electrically conductive trace to the surface of the synthetic polymer membrane.

In another embodiment, the electrically conductive material (e.g., electrically conductive ink) may be applied to the synthetic polymer membrane such that it is imbibed or otherwise incorporated into the microporous synthetic polymer membrane to place the electrically conductive material, and thus the conductive trace within the microporous synthetic polymer membrane and form a flexible printed circuit. "Imbibed" as used herein is meant to describe the inclusion and/or deposition of an electrically conductive material into the existing pores or void spaces of a microporous synthetic polymer membrane, typically via a liquid carrier (such as an electrically conductive ink) and specifically excludes filled membranes where the electrically conductive trace is an integral part of the synthetic polymer membrane and which may have some exposed electrically conductive trace within a pore or void space. It is to be noted that any known method of depositing electrically conductive material(s) into the pores or void spaces in a membrane may be utilized herein. In some embodiments, the electrically conductive trace occupies the pores through the thickness of a microporous synthetic polymer membrane. As such, the electrically conductive trace may occupy the majority of the pore volume in the microporous synthetic polymer membrane. In exemplary embodiments, the pores contain an amount of electrically conductive material that is sufficient to create a conductive trace for the passage of electrons therethrough.

The electrically conductive material may be applied to the synthetic polymer membrane by known deposition, coating methods, and imbibing methods such as, for example, screen printing, pad printing, flexographic printing, ink jet printing, and gravure printing to form the electrically conductive trace. The synthetic polymer membrane having thereon or therein an electrically conductive trace is referred to herein as a flexible printed circuit. Once a flexible printed circuit having the desired pattern of electrically conductive trace is formed, a dermally acceptable adhesive may be applied to the side of the synthetic polymer membrane opposing the electrically conductive trace. As used herein, the term "dermally acceptable adhesive" is meant to include adhesive materials that are natural or synthetic in origin and are formulated with ingredients that are generally recognized as safe when applied to the skin and which will adhere the flexible printed circuit (or flexible printed circuit board) to the skin such that it will remain on the skin for several days or weeks but will exhibit a necessary degree of release when the flexible printed circuit is intentionally removed so as not to tear or otherwise damage the skin. The dermally acceptable adhesives are skin-friendly, non-migratory, and have a variable degree of initial tack and peel and adhesion. A dermally acceptable adhesive should not include components or ingredients that may substantially irritate or damage healthy skin.

In some embodiments, the dermally acceptable adhesive is a pressure sensitive adhesive (PSA). Non-limiting examples of dermally acceptable adhesives include ARCARE® 7396 (a pressure-sensitive tape with MA-38 medical grade acrylic adhesive; Adhesives Research, Glen Rock, Pa.), acrylics, soft silicone gels, hydrogels, and hydrocolloids. The adhesives may be compounded with tackifiers and stabilizers as is well-known in the art.

Figure 14A:
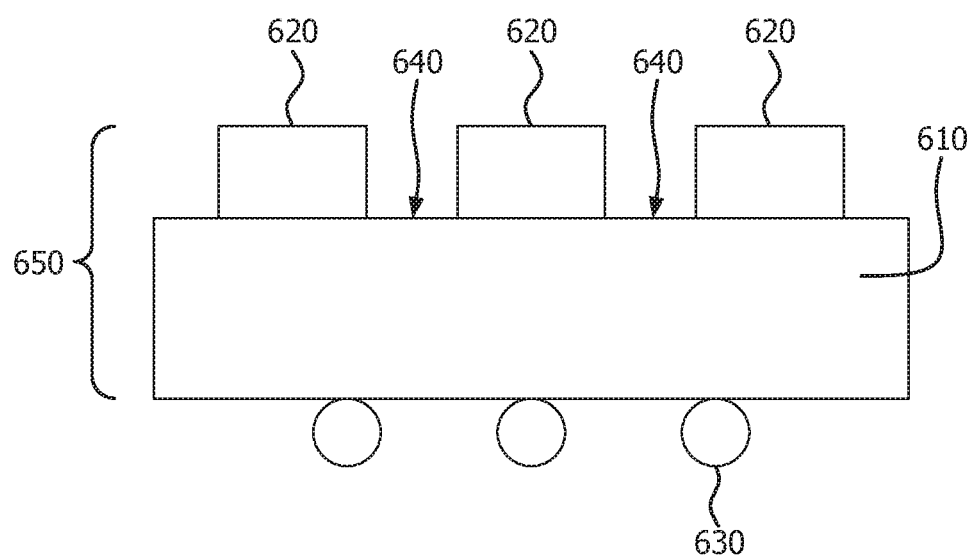
FIG. 14A is a schematic illustration of a flexible printed circuit having thereon a conductive trace and a discontinuous adhesive according to at least one embodiment.
Figure 14B:
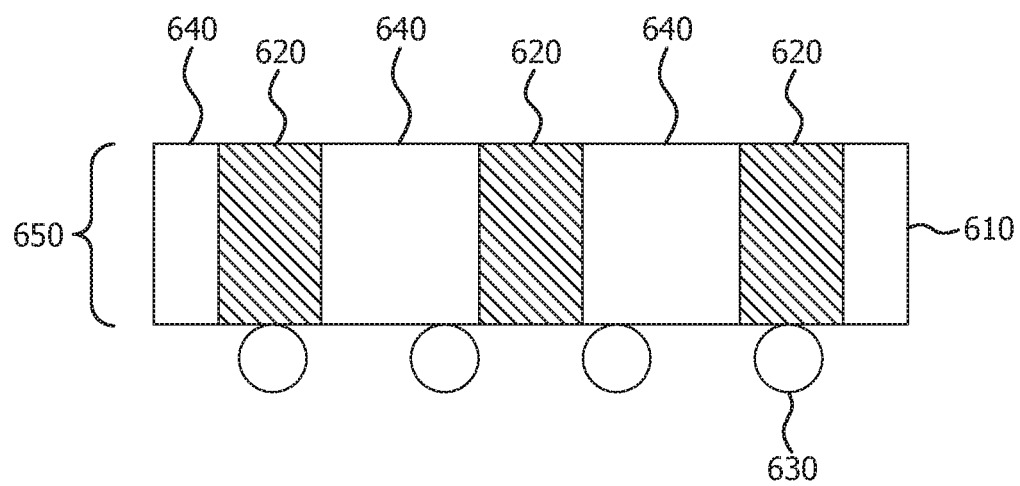
FIG. 14B is a schematic illustration of a flexible printed circuit having a conductive trace therein and a discontinuous adhesive according to at least one embodiment.

FIG. 14A illustrates a cross-sectional view of an embodiment where the conductive trace 620 has been applied to the surface of the synthetic polymer membrane 610, such as by printing the electrically conductive trace 620 on the microporous synthetic polymer membrane 610. In other embodiments as depicted in FIG. 14B, the conductive trace 620 has been imbibed or otherwise incorporated into the synthetic polymer membrane 610 to form the flexible printed circuit 650. Non-conductive regions 640 are positioned alongside the electrically conductive trace 620. In some embodiments, and as illustrated in FIGS. 14A and 14B, the dermally acceptable adhesive 630 may be applied to the flexible printed circuit 650 containing the synthetic polymer membrane 610 and the electrically conductive trace 620 in a gravure pattern in the form of adhesive dots 630.

Figure 14C:
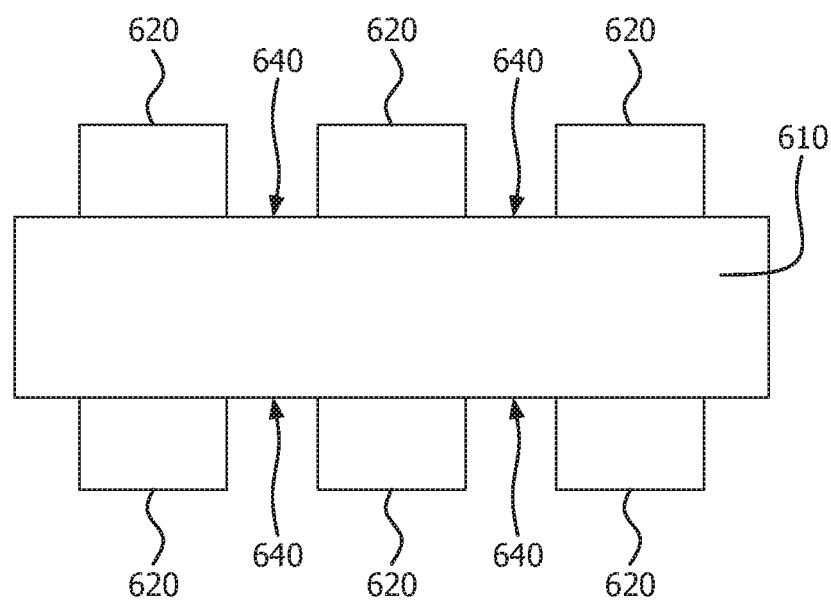
FIG. 14C is a schematic illustration of a flexible printed circuit with conductive traces on both sides of the synthetic polymer membrane according to at least one embodiment.
Figure 14D:
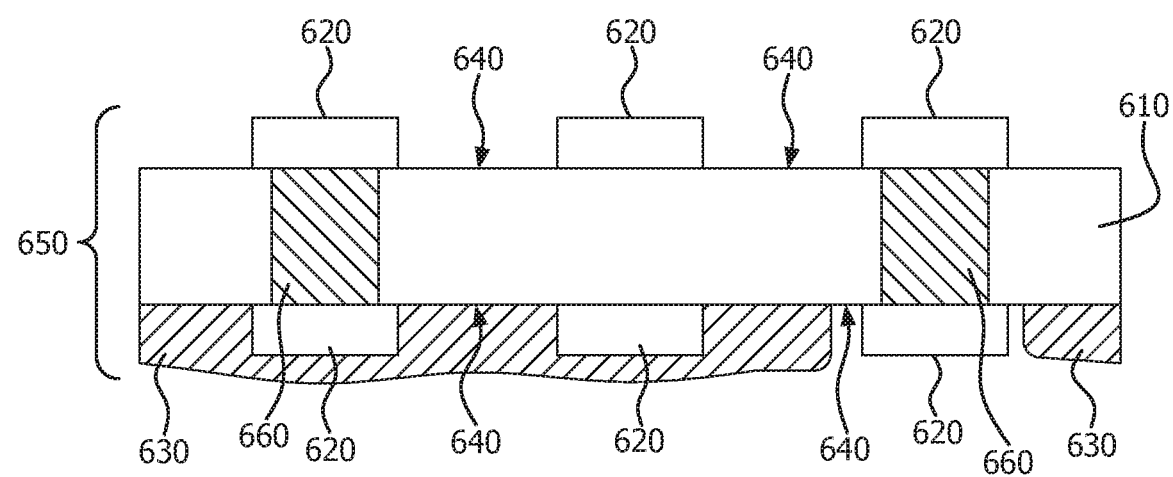
FIG. 14D is a schematic illustration of a flexible printed circuit with a dermally acceptable adhesive covering some of the electrically conductive according to at least one embodiment.

In an alternate embodiment (not depicted), the electrically conductive trace 620 may be applied to the synthetic polymer membrane 610 in a continuous manner so as to cover the surface of the synthetic polymer membrane 610. In a further embodiment, the electrically conductive trace 620 may be applied to both surfaces of the synthetic polymer membrane 610 in a discontinuous manner as shown in FIG. 14C. As depicted in FIG. 14D, the electrically conductive traces 620 communicate electrically with each other through one or more vertical interconnect access 660 (VIA). The VIA 660 may be formed by creating a through hole in the synthetic polymer membrane and filling the hole with electrically conductive material. Alternatively, the VIA may be formed by imbibing the electrically conductive material through the thickness of the porous synthetic polymer membrane, without the need to first create a through hole. As with the embodiments depicted in FIGS. 14A and 14B, non-conductive regions 640 are positioned alongside the electrically conductive trace 620 in FIGS. 14C and D. In the embodiment depicted in FIG. 14D, a dermally acceptable adhesive 630 covers some of the electrically conductive traces 620, while leaving other electrically conductive traces 620 exposed. The dermally acceptable adhesive 630 can be electrically insulating or electrically conductive, depending upon the requirements of the device and the desired electrical interaction with the skin.

It is to be appreciated that the pattern of the adhesive on the synthetic polymer membrane 610 is not limited so long as the flexible printed circuit 650 is able to bend in one or more directions (e.g., maintains flexibility). Thus, other adhesive patterns, such as grids, parallel lines, or continuous coatings are considered to be within the purview of the disclosure as long as the flexibility of the flexible printed circuit is maintained.

Once the flexible printed circuit 650 contains thereon or therein a dermally acceptable adhesive, such as adhesive dots 630, the flexible circuit 650 may be adhered to the skin of the user. In use, the flexible circuit may be electrically coupled with an electronic member selected from a resistor, a capacitor, a light emitting diodes (LED), an integrated circuit, a sensor, a power source, a data transmitter, or a data receiver, etc. (depending on the desired end use) to form a flexible printed circuit board. As used herein, a flexible printed circuit board is meant to include a flexible printed circuit having one or more electronic component electrically connected (coupled) thereto. Once the data is collected, for example, the user may remove the flexible circuit 650 by pulling on the synthetic polymer membrane 610 and peeling the flexible circuit 650 off of the skin.

Figure 7:
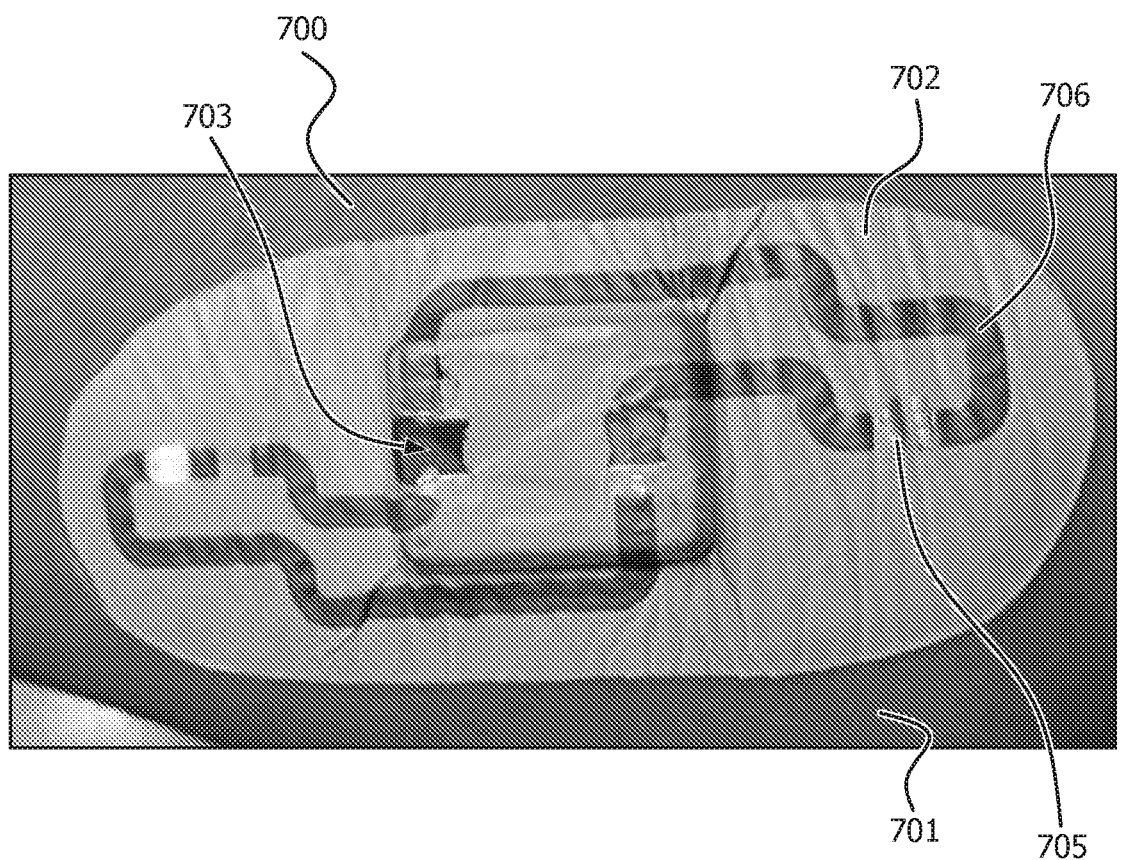
FIG. 7 is an image of an exemplary hybrid flexible printed circuit board for dermal applications according to at least one embodiment.

In another embodiment, depicted in FIG. 7, an electronic module 703 may be physically and electrically connected (coupled) to the conductive trace positioned on the surface of the microporous synthetic polymer membrane 702 (e.g., flexible printed circuit or flexible printed circuit board) to form a hybrid flexible printed circuit board 700. An electronic module is defined herein as an assembly that includes more than two or more electronic components that are electrically coupled. An insulative overcoat 706 may be positioned over all or portions of the conductive trace. It is to be appreciated that an imbibed conducive trace may alternatively be used. In use, the flexible printed circuit board 700 interfaces electrically with the electronic module 703. Also, in at least one embodiment, the electronic module 703 may be positioned between the synthetic polymer membrane 702 and the skin 701. Such a positioning of the electronic module 703 creates a very durable device that is resistant to damage during use. Covering the electronic module with the synthetic polymer membrane 702 reduces or even minimizes the risk of catching the edge of the module and peeling it off as the user engages in activities or otherwise engages with the environment. The generally slippery nature of synthetic polymer membranes, especially expanded polytetrafluoroethylene (ePTFE), creates a low friction interface between the device and the wearer's clothing, giving the wearer the ability to move freely with the flexible printed circuit board discretely located on a portion of the body that may be hidden by clothing. In some embodiments, an insulative overcoat 706 may be applied over the electrically conductive trace 705 to assist in protecting the electrically conductive trace 705 from external elements, such as, but not limited to, abrasion and water. It is to be noted that an insulative overcoat may be applied over any conductive trace described herein. Non-limiting examples of materials used to form the insulative overcoat include urethanes, acrylics, silicones, Styrene Isoprene Butadiene Block Copolymers, Viton™ FKM (a synthetic rubber and fluoropolymer elastomer), polyolefins, or fluoropolymers.

Although not depicted in any figure, it is to be appreciated that some conductive trace may be located on the surface of a porous synthetic polymer membrane as a consequence of the imbibing process. In embodiments where the conductive trace is applied via a liquid carrier (e.g. an electrically conductive ink) heat may be applied to the flexible printed circuit to remove the liquid carrier. The temperature applied may be sufficient to at least partially fuse the conductive trace (e.g., metal particles) in the synthetic polymer membrane to form a continuous network of conductive particles. In other embodiments, such as where the conductive trace is applied to the surface of the microporous synthetic polymer membrane, heat may be applied to at least partially melt the conductive trace (e.g., metal particles) to form a continuous network of conductive particles on the surface of the synthetic polymer membrane. At least partial melting the conductive trace is one way to establish electrical conductance of the conductive trace. In further embodiments, heat may be used to remove ligands or other processing aids from the conductive particles.

Advantageously, the flexible printed circuits described herein are highly flexible, having a flexibility of less than about 1.0 newton as evidenced by the Peak Compression Load Test (Compressive Buckling) test method set forth below. In some embodiments, the flexibility is less than about 0.9 newtons, less than about 0.8 newtons, less than about 0.7 newtons, less than about 0.6 newtons, less than about 0.5 newtons, less than about 0.4 newtons, less than about 0.3 newtons, less than about 0.2 newtons, or less than about 0.1 newton. In addition, the flexible printed circuits are extremely durable, where the load applied to cause a 2× increase in resistance is greater than about 6.0 newtons when tested according to the Load Required to Double the Resistance Test set forth below. In some embodiments, the load is greater than about 0.7 newtons, greater than about 1.0 newtons, greater than about 1.4 newtons, greater than about 2.0 newtons, greater than about 3.0 newtons, or greater than about 5.0 newtons. The flexible circuit board is also comfortable, as evidenced by the On Skin Comfort Test below, which received scores in the most comfortable range.

The flexible printed circuits, the flexible printed circuit board, and the hybrid flexible printed circuit board reach a balance of comfort, flexibility, and durability. For instance, materials such as PET and Kapton are not comfortable, but are durable. Also, soft and comfortable materials such as urethanes are not durable. Also, stiff materials such as Mylar® (i.e., polyethylene terephthalate (PET)) or Kapton are durable, but not flexible.

Test Methods

It should be understood that although certain methods and equipment are described below, other methods or equipment determined suitable by one of ordinary skill in the art may be alternatively utilized.

ATEQ Airflow

ATEQ Airflow is a test method for measuring laminar volumetric flow rates of air through membrane samples. For each membrane, a sample was clamped between two plates in a manner that seals an area of 2.99 cm$^2$ across the flow pathway. An ATEQ® (ATEQ Corp., Livonia, Mich.) Premier D Compact Flow Tester was used to measure airflow rate (L/hr) through each membrane sample by challenging it with a differential air pressure of 1.2 kPa (12 mbar) through the membrane.

Gurley Airflow

The Gurley air flow test measures the time in seconds for 100 cm$^3$ of air to flow through 1 in$^2$ (~6.45 cm$^2$) sample at 0.177 psi (~1.22 kPa) of water pressure. The samples were measured in a GURLEY™ Densometer and Smoothness Tester Model 4340 (Gurley Precision Instruments, Troy, N.Y.). The values reported are an average of 3 measurements and are in the units of seconds.

Non-Contact Thickness

Figure 17A:
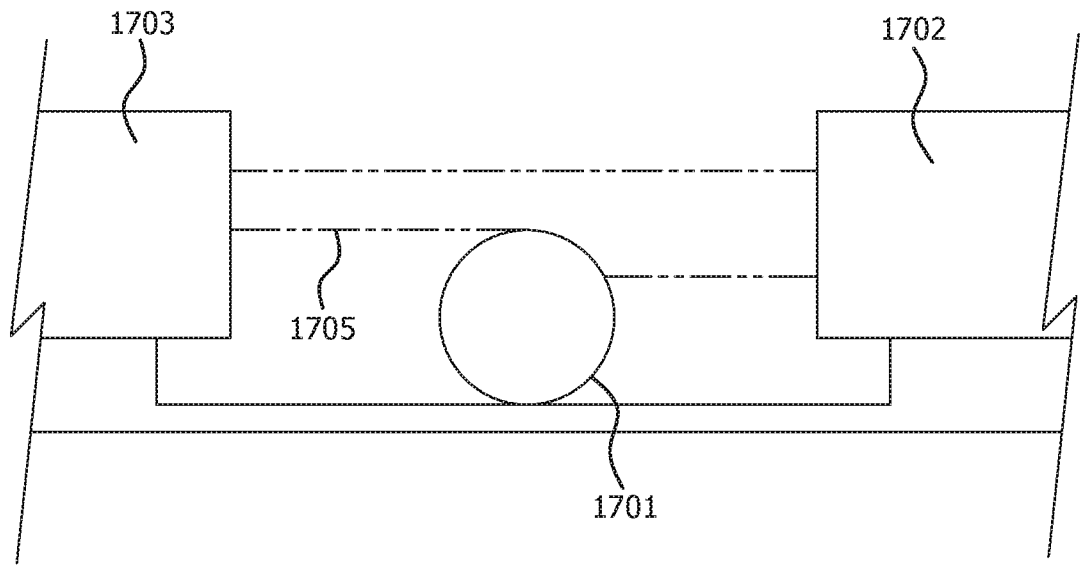
FIG. 17A is a schematic illustration of a metal cylinder aligned between a laser micrometer source and a laser micrometer receiver for measuring thickness of the synthetic polymer membrane when using a laser micrometer according to at least one embodiment.
Figure 17B:
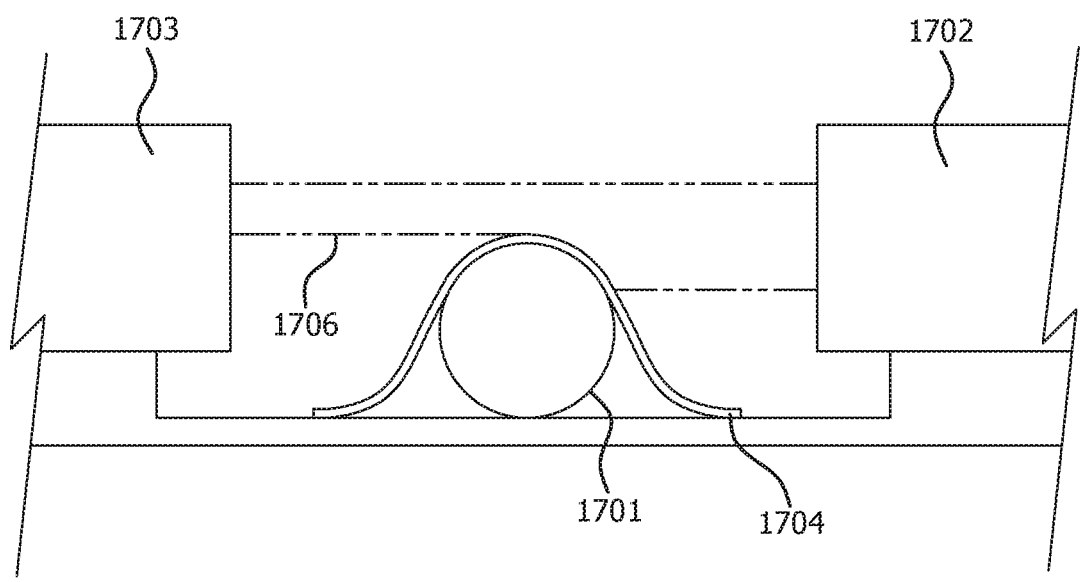
FIG. 17B is a schematic illustration of a single layer of membrane draped over the surface of the metal cylinder shown in FIG. 12A without overlap and without wrinkles when measuring the thickness of the synthetic polymer membrane when using a laser micrometer according to at least one embodiment.

Non-contact thickness was measured using a laser micrometer (Keyence model no. LS-7010, Mechelen, Belgium). As shown in FIGS. 17A and B, a metal cylinder 1701 was aligned between a laser micrometer source 1702 and a laser micrometer receiver 1703. The shadow 1705 of the top of the cylinder 1701 is projected onto receiver 1703 as shown in FIG. 17A. The position of the shadow was then reset as the "zero" reading of the laser micrometer. As shown in FIG. 17B, a single layer of membrane 1204 is draped over the surface of the metal cylinder 1701 without overlap and without wrinkles, casting shadow 1706 onto the receiver 1703. The laser micrometer then indicated the change in the position of the shadows 1705 and 1706 as the thickness of the sample. Each thickness was measured three times and averaged for each sample.

Mass Per Area (Mass/Area)

The mass per area of samples was measured according to the ASTM D 3776 (Standard Test Methods for Mass Per Unit Area (Weight) of Fabric) test method (Option C) using a Mettler-Toledo Scale, Model 1060. The scale was recalibrated prior to weighing specimens, and the results were reported in grams per square meter (g/m$^2$).

Moisture Vapor Transmission Rate (MVTR) Measurement for Skin Contact Samples

Approximately 70 mL of a solution consisting of 35 parts by weight of potassium acetate and 15 parts by weight of distilled water was placed into a 133-mL polypropylene cup having an inside diameter of 6.5 cm at its mouth. An expanded polytetrafluoroethylene (ePTFE) membrane having a minimum MVTR of approximately 85,000 g/m$^2$/24 hr as tested by the method described in U.S. Pat. No. 4,862,730 to Crosby, was attached to the lip of the cup using a rubber band to create a taut, leak-proof, microporous barrier containing the solution, creating a cup assembly.

A similar expanded polytetrafluoroethylene (ePTFE) membrane having an MVTR of approximately 85,000 g/m$^2$/24 hr as tested by the method described in U.S. Pat. No. 4,862,730 to Crosby was mounted to the surface of a water bath. The water bath assembly was controlled at 23±0.2° C., utilizing a temperature controlled room and a water circulating bath.

A sheet of office paper was cut to 180 mm square with a 90 mm diameter hole in the center. Release paper on an adhesive backed flexible printed circuit was removed while the substrate was supported in a hoop, and the office paper was applied to the adhesive so that the printed pattern was approximately centered within the 90 mm hole in the office paper. The flexible printed circuit was then removed from the hoop. The office paper support allowed the flexible printed circuit to be more easily handled during testing. Excess substrate was trimmed and discarded.

The adhesive-backed flexible printed circuit with a paper boarder was placed adhesive side up onto the expanded polytetrafluoroethylene membrane mounted to the surface of the water bath and allowed to equilibrate for at least 15 minutes prior to the introduction of the cup assembly.

The expanded polytetrafluoroethylene end of the cup assembly was pressed against the adhesive, which was approximately centered within the hole in the support paper. The cup and sample were quickly removed from the water bath, weighed to the nearest 1/1000 g, and placed back into the water bath.

Water transport was provided by the driving force between the water in the water bath and the saturated salt solution providing water flux by diffusion in that direction. The sample rested for 60 minutes and the cup assembly was then removed, weighed again within 1/1000 g.

The moisture vapor transmission rate (MVTR) of the sample was calculated from the weight gain of the cup assembly and was expressed in grams of water per square meter of sample surface area per 24 hours.

Matrix Tensile Strength Determination

A synthetic polymer membrane was cut in each the longitudinal and transverse directions using an ASTM D412-Dogbone F. The "machine direction" is in the direction of the extrusion and the "transverse direction" is parallel to this. The membrane was placed on a cutting table such that the membrane was free from wrinkles in the area in which the membrane was to be cut. A die was then placed on the membrane (generally in the center 200 mm of the membrane) such that its long axis was parallel to the direction that would be tested. Once the die was aligned, pressure was applied to cut through the synthetic polymer membrane. Upon removal of the pressure, the dogbone sample was inspected to ensure it was free from edge defects which may impact the tensile testing. At least 3 dogbone samples in the machine direction and three dogbone samples in the transverse direction were prepared in this manner. Once the dogbone samples were prepared, they were measured to determine their mass using an analytical balance and their thickness using a Mitutoyo 547-400S thickness gauge.

Tensile break load was measured using an INSTRON® 5500R (Illinois Tool Works Inc., Norwood, Mass.) tensile test machine equipped with a rubber coated face plate and a serrated face plate such that each end of the dogbone sample was held between one rubber coated plate and one serrated plate. The pressure applied to the grip plates was approximately 552 kPa. The gauge length between the grips was set at 58.9 mm and the crosshead speed (pulling speed) was set to a speed of 508 mm/min. A 500 N load cell was used to carry out these measurements and data was collected at a rate of 50 points/sec. The laboratory temperature was between 20° C. and 22.2° C. to ensure comparable results. If the dogbone sample broke at the grip interface, the data was discarded. At least three dogbone samples in the machine direction and three dogbone samples in the transverse direction were successfully pulled (i.e., no slipping out of or breaking at the grips) in order to characterize the dogbone samples.

The following equation was used to calculate the matrix tensile strength:

$$MTS = ((F\max/w)^* p)/mass:area, \text{ in which:}$$

$MTS$ = matrix tensile strength in MPa, $F\max$ = maximum load measured during test(newtons), $w$ = width of *dogbone* sample within the gauge length (meters), $p$ = density of *PTFE* ($2.2 \times 10^6$ g/m$^3$) or density of polyethylene (0.94 g/m$^3$), and mass:area = mass per area of the sample (g/m$^3$).

Bubble Point

Bubble point pressures were measured according to the general teachings of ASTM F31 6-03 using Porometer (Model 3Gzh from Quantachrome Instruments, Boynton Beach, Fla.). The sample membrane was placed into the sample chamber and wet with Silwick Silicone Fluid (available from Porous Materials Inc.) having a surface tension of 20.1 dynes/cm. The bottom clamp of the sample chamber had a 2.54 cm diameter, 0.159 cm thick porous metal disc insert (Quantachrome part number 75461 stainless steel filter) and was used to support the sample. Using the 3GWin software version 2.1, the following parameters were set as specified in the table immediately below. The values presented for bubble point pressure are the average of two measurements. Bubble point pressure was converted to pore size using the following equation:

$$DBP = 4\gamma lv \cos \ominus /PBP$$

where DBP is the pore size, γlv is the liquid surface tension, ⊖ is the contact angle of the fluid on the material surface, and PBP is the bubble point pressure. It is understood by one skilled in the art that the fluid used in a bubble point measurement must wet the surface of the sample.

| Bubble Point Instrument Settings | |
|---|---|
| Parameter | |
| Run Settings | |
| Starting pressure | 2.12 psig |
| Ending pressure | 85.74 psig |
| Sample Area | 3.14 cm$^2$ |
| Run Type | Wet Only |
| Number Data Points | 256 |
| Pressure Control | |
| Use Normal Equilibrium | TRUE |
| Use Tol | FALSE |
| Use Time | FALSE |
| Use Rate | FALSE |
| Use Low Flow Sensor | FALSE |
| Time Out | NA |
| Equil Time | NA |
| Run Rate | NA |
| Pressure Tolerance | NA |
| Flow Tolerance | NA |

-continued

| Bubble Point Instrument Settings | |
|---|---|
| Parameter | |
| Smoothing | |
| UseMovAve | FALSE |
| MovAveWet Interval | NA |
| MovAveDry Interval | NA |
| Lowess Dry | 0.050 |
| Lowess Wet | 0.050 |
| Lowess Flow | 0.050 |
| Lowess Num | 0.100 |
| MinSizeThreshold | 0.98 |
| Bubble Point Parameters | |
| UseBpAuto | TRUE |
| UseBpThreshold (L/min) | FALSE |
| UseBpThreshold (Abs/cm2) | FALSE |
| UseBpThresholdNumber | FALSE |
| BpAutoTolerance (manual) | 1% |
| BpThresholdValue (manual) | NA |
| Bp Threshold (abs/cm2) value | 0 |

Load Required to Double the Resistance Test

A flexible printed circuit was placed in a mechanical property testing machine (INSTRON® Model 5965, Illinois Tool Works Inc., Glenview, Ill.). The flexible printed circuit was stretched and the load (newtons) required to achieve a doubling of the resistance was measured.

Figure 4:
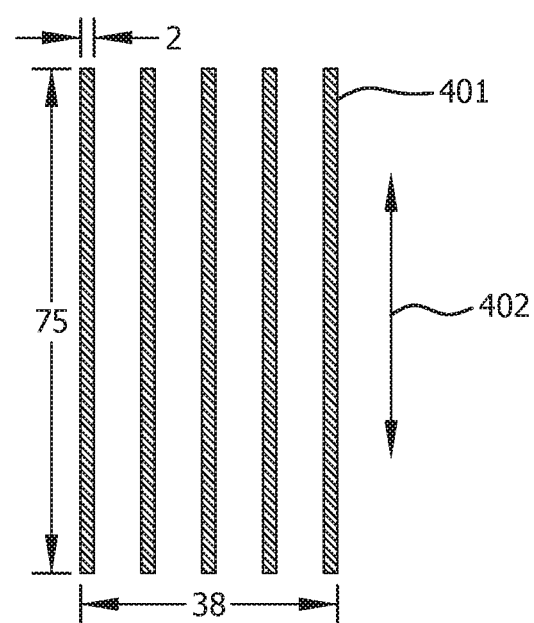
FIG. 4 is a graphical illustration of the arrangement and size of exemplary conductive traces used in Examples according to at least one embodiment.

An adhesive backed flexible printed circuit was trimmed so that a single printed conductive line 401 shown in FIG. 4 was centered within a 15 mm wide strip. The grips of the INSTRON® Model 5965 were positioned 100 mm apart and the flexible printed circuit was gripped so that the printed feature (conductive line) was roughly centered within the gap. Matching source and sense leads of a KEITHLY® 580 micro ohmmeter were each connected to the two ends of the printed line 401 and the load cell was zeroed. The flexible printed circuit was strained using a crosshead speed of 10 mm/minute. Resistance of the conductive trace and the load applied to the flexible printed circuit were captured concurrently. As the test progressed, the resistance of the conductive trace increased. The load applied to the flexible printed circuit when the resistance reached a value that was double the initial resistance was recorded and reported in newtons.

Peak Compression Load Test (Compressive Buckling)

Figure 6:
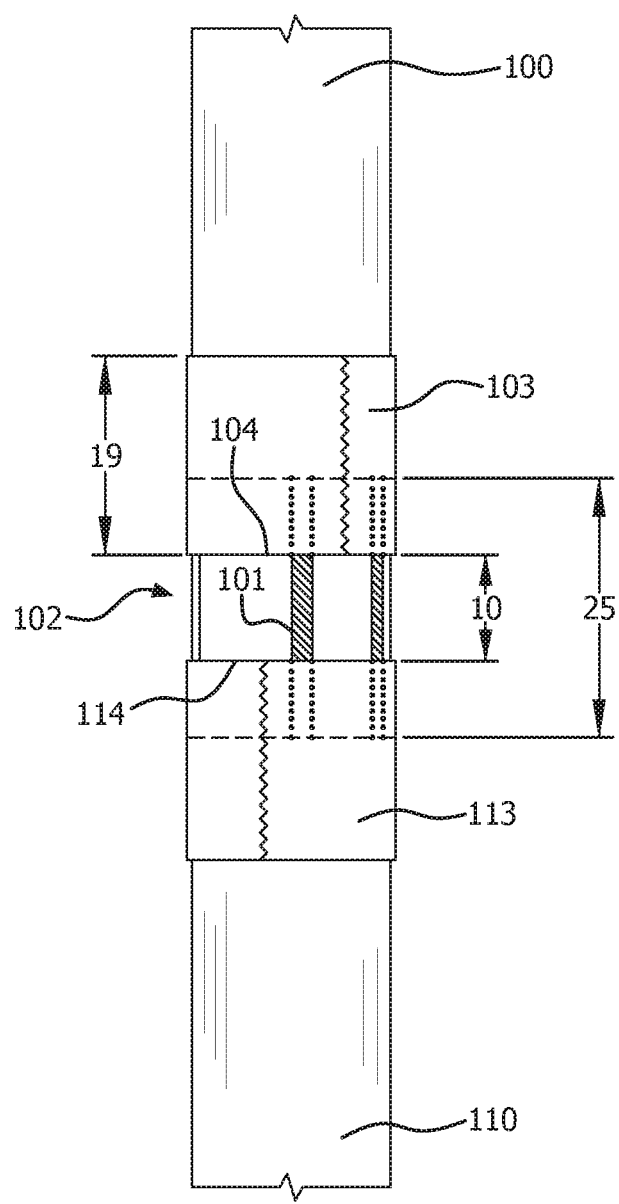
FIG. 6 is a schematic illustration of the compression testing device used in the Test Method entitled "Peak Compression Load Test (Compressive Buckling)" according to at least one embodiment.

Two 15 mm diameter aluminum cylinders 100, 110 as shown in FIG. 6 were fabricated and mounted in an INSTRON® Model 5965 so that the cylinders were concentric, with one cylinder attached to the frame and the other attached to the crosshead. The free edges 104, 114 of the cylinders were positioned 10 mm apart, and the 100 N load cell on the crosshead was zeroed.

An adhesive backed flexible printed circuit 102 having thereon a release liner was prepared by removing the release paper and dusting the adhesive with powdered talc. The talc eliminated the tackiness of the adhesive without significantly affecting the mechanical properties of the flexible printed circuit, and made the flexible printed circuit 102 easier to handle. The flexible printed circuit 102 was then cut to a size of 70 mm×25 mm with the printed features 101 parallel to the shorter side and approximately centered with respect to the longer side. The flexible printed circuit 102 was wrapped around the aluminum cylinders 100, 110, spanning the 10 mm gap and overlapping each cylinder 100, 110 by approximately 7.5 mm as shown in FIG. 6. The flexible printed circuit 102 was attached to the cylinders 100, 110 using 19-mm wide paper tape 103, 113 (89097-990, VWR Scientific (a division of Avantor), Radnor, Pa.) in a manner that minimized wrinkles in the flexible printed circuit 102. One edge of the tape 103 was aligned with the free edge 104 of the aluminum cylinder 100. One edge of the tape 113 was aligned with the free edge 114 of the other aluminum cylinder 110. A 10 mm gap was maintained between the aluminum cylinders 100, 110 in which only the flexible printed circuit 102 was present.

Prior to testing, the aluminum cylinders 100, 110 were positioned so that a tensile load between 0.5 N and 1.5 N was applied to the flexible printed circuit 102. The crosshead was then moved at a rate of 10 mm/min until the distance between the free edges 104, 114 of the aluminum cylinders 100, 110 was reduced to 5 mm. The peak compressive load required to compress and buckle the flexible printed circuit 102 was recorded. This test was performed on three different specimens from the same flexible printed circuit 102 and the average of these three tests was recorded and reported in Newtons.

On-Skin Comfort Test

Figure 5:
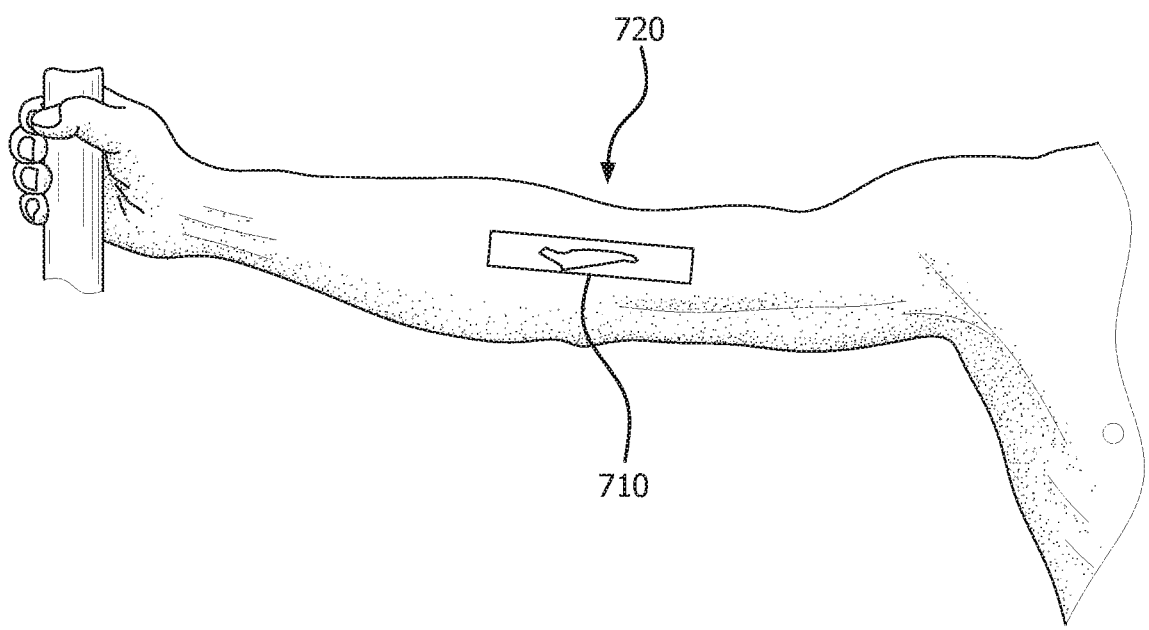
FIG. 5 is a sketch depicting the location of a flexible printed circuit board applied to the inner surface of the elbow during comfort testing according to at least one embodiment.

An adhesive backed flexible printed circuit with a release liner was trimmed to a rectangular shape that was 90 mm long and 25 mm wide. A 25 mm wide strip of polyester tape 8992 (3M, St Paul, Minn.) was applied to the printed side of the flexible printed circuit to act as a transfer tape during application. The skin within and around the cubital fossa (interior bend of elbow) of a volunteer was prepared by wiping the skin with an alcohol prep pad and allowing the skin to dry. The paper release liner was removed from the flexible printed circuit 710 and the exposed adhesive (not illustrated) was applied to the volunteer's arm so that it crossed the cubital fossa 720 and was approximately oriented as depicted in FIG. 5. The polyester tape was carefully removed, leaving the flexible printed circuit 710 (i.e., synthetic polymer membrane with conductive traces thereon) adhered to the skin. One inventive flexible printed circuit 710 was applied to one arm and a comparative printed circuit (not illustrated) made in accordance with Example 7 was applied to the other arm of each volunteer. The volunteer was asked to wear the flexible printed circuits for up to 8 hours, and to rank the comfort on a scale of 1 to 10, where 1 was the least comfortable, and 10 was the most comfortable. The ranking guidelines proposed to each volunteer were as follows:

| Comfortable Range | 10 | Most comfortable. Could barely feel it, easy to forgot about it |
|---|---|---|
| | 9 | |
| | 8 | Occasionally noticed it during extreme activities or motions |
| | 7 | |
| | 6 | Occasionally noticed it during routine activities. Don't mind wearing it |
| Uncomfortable Range | 5 | Occasionally noticed it during routine activities. Would prefer not to wear it. |
| | 4 | |
| | 3 | Regularly noticed it, irritating, eager to remove it |
| | 2 | |
| | 1 | Least comfortable. Noticed it constantly; caused significant irritation; very eager to remove it, or removed it early |

The results reported are an average of at least 4 tests.

ePTFE Membranes ePTFE Membrane 1—Preparation ePTFE Membrane

An ePTFE membrane was manufactured according to the general teachings set forth in U.S. Patent Publication No.

2004/0173978 to Bowen et al. The ePTFE membrane had a mass-per-area of 4.6 g/m², a porosity of 87%, a non-contact thickness of 15.5 µm, a Gurley number of 4.5 seconds, an ATEQ air flow of 17 liters/cm²/hour at 12 mbar, a matrix tensile strength of 258 MPa in the machine direction, a matrix tensile strength of 329 MPa in the transverse direction, a specific surface area of 14.520 m²/g, and a surface area per volume of 31.944 m²/cm³. A scanning electron microscope (SEM) image of the ePTFE membrane is shown in FIG. 1.

ePTFE Membrane 2—Preparation ePTFE Membrane

Figure 2:
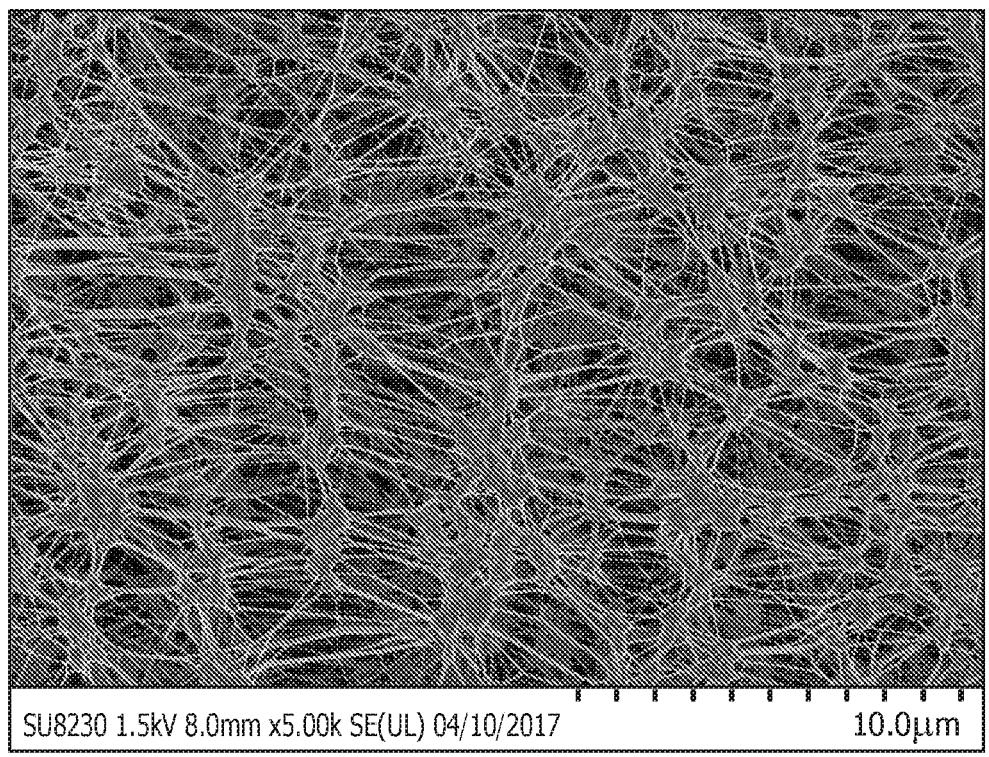
FIG. 2 is an SEM of a microporous expanded polytetrafluoroethylene (ePTFE) membrane (Membrane 2) according to at least one embodiment.

An ePTFE membrane was manufactured according to the general teachings set forth in U.S. Pat. No. 3,953,566 to Gore. The ePTFE membrane had a mass-per-area of 16.6 g/m², a porosity of 80%, a non-contact thickness of 37.6 µm, a bubble point of 156 kPa, a matrix tensile strength of 42.4 MPa in the machine direction, a matrix tensile strength of 116.4 MPa in the transverse direction, a specific surface area of 7.891 m²/g and a surface area per volume of 17.75 m²/cm³. An SEM image of the ePTFE membrane is shown in FIG. 2.

EXAMPLES

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

Example 1

A flexible printed circuit was manufactured and combined with a dermally acceptable adhesive. Expanded polytetrafluoroethylene (ePTFE) membrane (Membrane 1) was used as substrate for printing.

To prepare the ePTFE for imbibing, the ePTFE membrane was restrained by laying it over a 6-inch diameter aluminum hoop, fixing it to the hoop by placing a stainless steel spring around the circumference, and tensioning the substrate to remove wrinkles. To support the ePTFE membrane during adhesion of a stencil, the hoop restraining the ePTFE membrane was placed over a clean DELRIN® (an acetal homopolymer resin available from DowDuPont, Wilmington, Del.) disc that was machined to fit inside the hoop, and which provided a clean surface that contacted the "bottom" of the ePTFE membrane.

To prepare the stencil, a piece of tape (Scapa Type 536; a polyester film, single coated with an acrylic adhesive; Scapa North America, Windsor, Conn.) was transferred to the release paper, and a laser cutter (PLS6.75 laser cutter, Universal Laser, Scottsdale, Ariz.) was used to cut holes in the tape stencil in the pattern shown in FIG. 4. The dimensions shown in FIG. 4 are in mm and are shown for to indicate the size of the pattern. The double ended arrow 402 is shown to illustrate the alignment of the ePTFE membrane with the conductive trace.

The tape stencil was then removed from the release paper and pressed by hand to the surface of the exposed "top" surface of the ePTFE membrane to firmly adhere the stencil to the ePTFE membrane. The tape stencil was oriented on the ePTFE membrane so that the arrow 402 in FIG. 4 was aligned with the transverse direction of the ePTFE membrane. The stencil and ePTFE membrane, still restrained on the hoop, were then removed from the DELRIN® disc and placed in a laboratory fume hood for imbibing. An excess of conductive ink (2108-IPA available from Nanogap, Inc.) was pipetted onto the top surface of the ePTFE membrane through the holes in the tape stencil. When this process was complete, the top surface of the stencil/ePTFE membrane was thoroughly wiped with a cellulose fiber wiper (KIM-WIPES®; Kimberly Clark, Delicate Task Wiper, 1-ply) to remove any excess ink. The tape stencil was then promptly removed. Removal of the stencil also removed a portion of the upper surface of the ePTFE membrane that was adhered to the stencil, but the amount was considered negligible. The imbibed ePTFE membrane (flexible printed circuit), still restrained in the hoop, was then allowed to air dry in the hood for at least 10 minutes, and then heat-treated in a hot air convection oven for 60 minutes at 200° C.

Dermal Adhesive and Lamination

A dermally acceptable adhesive, ARCARE®7396 (a pressure-sensitive tape with MA-38 medical grade acrylic adhesive; Adhesives Research, Glen Rock, Pa.) was selected. The adhesive was provided on a roll supported by paper release liner. The release liner with adhesive was cut into a square at least 130 mm×130 mm and applied by hand to the side of the ePTFE membrane opposing the side on which the conductive ink was applied. The printed pattern was approximately centered relative to the adhesive. With the eTPFE membrane supported by a lab bench, pressure was applied by hand to the release paper, pressing the adhesive firmly to the printed flexible circuit.

Load Required to Double the Resistance Test

The flexible printed circuit was tested using the Load Required to Double the Resistance Test described in the Test Method section set forth above. The load applied to cause a 2× increase in resistance was determined to be 1.49 Newtons (Table 1).

MTVR

The moisture vapor transmission rate was measured as described in the test method entitled "Moisture Vapor Transmission Rate (MVTR) Measurement for Skin Contact Samples" set forth above. The MVTR was determined to be 593 g/m²/24 hours (Table 1).

Peak Compression Load Test

The peak load measured was measured as described in the test method entitled "Peak Compression Load Test (Compressive Buckling)". The peak load was determined to be 0.0471 Newtons (Table 1).

Example 2

A flexible printed circuit was manufactured and combined with a dermally acceptable adhesive. Expanded polytetrafluoroethylene membrane (Membrane 1) was used as substrate for printing.

Surface-Printing Conductive Traces onto a Substrate for Skin Contact

The ePTFE membrane was restrained in a 356 mm diameter embroidery hoop, tensioned to remove wrinkles, and screen-printed using conductive ink in the pattern shown in FIG. 4. The dimensions shown in FIG. 4 are in mm and are shown to indicate the size and shape of the pattern. The double ended arrow 402 is shown to illustrate the alignment of the ePTFE membrane with the conductive trace. The conductive ink used was CI1036 (Engineered Conductive Materials, Delaware, Ohio). The ink was thinned with 8.7% methyl ethyl ketone (MEK) by weight prior to printing. The screen printing was performed using a model MSP-088 screen printer (HMI Manufacturing, Lebanon, N.J.), a stainless steel screen with 200 TPI (threads/wire per inch; ~78.74 wires per cm), 1.6 mil (~40.64 μm) wire diameter, and a 12.7 micron emulsion of the ink. The printing was performed so that the arrow 402 in FIG. 4 was aligned with the transverse direction of the ePTFE membrane. After printing the ink was then dried in a convection oven at 120° C. for 20 minutes.

Dermal Adhesive and Lamination

Dermal adhesive and lamination was conducted according the process described in Example 1.

Load Required to Double the Resistance Test

The flexible printed circuit was tested using the Load Required to Double the Resistance Test described in the Test Method section set forth above. The load applied to cause a 2× increase in resistance was determined to be 2.3788 Newtons (Table 1).

MTVR

The moisture vapor transmission rate was measured using the test method entitled "Moisture Vapor Transmission Rate (MVTR) Measurement for Skin Contact Samples" set forth herein. The MVTR was determined to be 586 g/m²/24 hours (Table 1).

Peak Compression Load Test

The peak load was measured as described in the test method entitled "Peak Compression Load Test (Compressive Buckling)" set forth above. The peak load was determined to be 0.0815 Newtons (Table 1).

Example 3

A flexible printed circuit was manufactured and combined with a dermally acceptable adhesive. Expanded polytetrafluoroethylene (ePTFE) membrane (ePTFE Membrane 2) was used as the substrate for printing.

Surface-Printing Conductive Traces onto a Substrate for Skin Contact

Surface printing of the conductive trace on the ePTFE substrate was conducted using the procedure described in Example 2.

Dermal Adhesive and Lamination

Dermal adhesive and lamination was conducted according the process described in Example 1.

Load Required to Double the Resistance Test

The flexible printed circuit was tested using the Load Required to Double the Resistance Test described in the Test Method section set forth above. The load applied to cause a 2× increase in resistance was determined to be 1.5183 Newtons (Table 1).

MTVR

The moisture vapor transmission rate was measured using the test method entitled "Moisture Vapor Transmission Rate (MVTR) Measurement for Skin Contact Samples" set forth herein. The MVTR was determined to be 745 g/m²/24 hours (Table 1).

Peak Compression Load Test

The peak load was measured as described in the test method entitled "Peak Compression Load Test (Compressive Buckling)" set forth above. The peak load was determined to be 0.1432 Newtons (Table 1).

On-Skin Comfort Test

On-skin comfort was determined utilizing the test method entitled "On-Skin Comfort Test" set forth above. The average rank score for the printed circuit was determined to be 8.5 (Table 1).

Example 4

Figure 3:
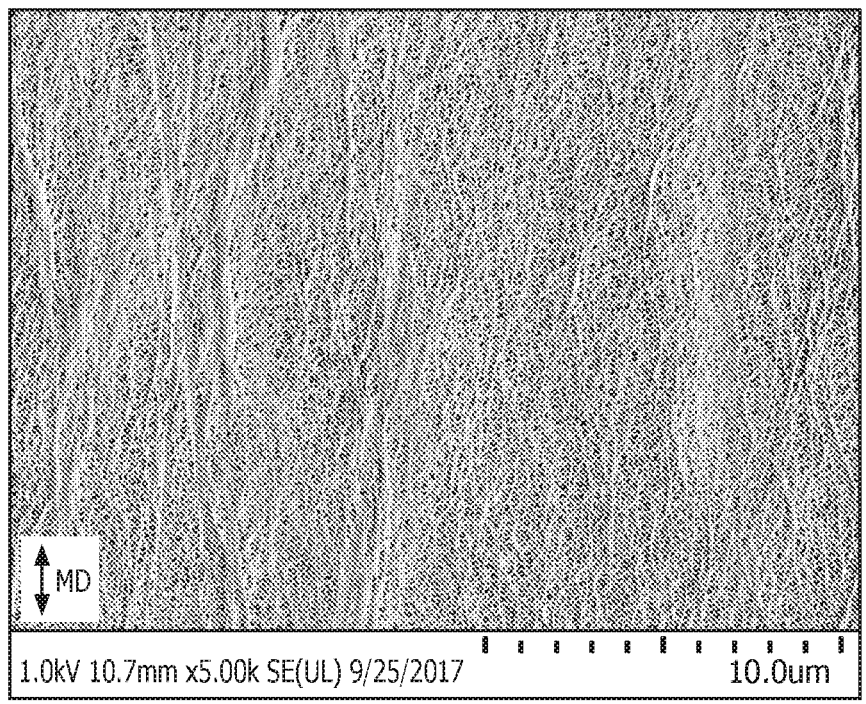
FIG. 3 is an SEM of the microporous polyethylene lithium ion battery insulation membrane utilized in Example 4 according to at least one embodiment.

A flexible circuit was manufactured and combined with a dermally acceptable adhesive. A porous polyethylene lithium ion battery insulation membrane, (Pair Materials Co. Ltd, Dongguan, China) was obtained and used as the printing substrate. The polyethylene membrane had a mass-per-area of 7.0 g/m², a porosity of 40%, a thickness of 12.4 μm, a bubble point of 1543 kPa, a matrix tensile strength of 314 MPa in the machine direction, a matrix tensile strength of 233 MPa in the transverse direction, a gravimetric specific surface area of 34.1 m²/g, and a volumetric specific surface area of 32.1 m²/cm³. An SEM image of the membrane is shown in FIG. 3.

Surface-Printing Conductive Traces onto a Substrate for Skin Contact

Surface printing of the conductive trace on the polyethylene (PE) substrate was conducted using the procedure described in Example 2.

Dermal Adhesive and Lamination

Dermal adhesive and lamination was conducted according the process described in Example 1.

Load Required to Double the Resistance Test

The flexible printed circuit was tested using the Load Required to Double the Resistance Test described in the Test Method section set forth above. The load applied to cause a 2× increase in resistance was determined to be 5.6267 Newtons (Table 1).

MTVR

The moisture vapor transmission rate was measured using the test method entitled "Moisture Vapor Transmission Rate (MVTR) Measurement for Skin Contact Samples" set forth herein. The MVTR was determined to be 340 g/m²/24 hours (Table 1).

Peak Compression Load Test

The peak load was measured as described in the test method entitled "Peak Compression Load Test (Compressive Buckling)" set forth above. The peak load was determined to be 0.5826 Newtons (Table 1).

On-Skin Comfort Test

On-skin comfort was determined utilizing the test method entitled "On-Skin Comfort Test" set forth above. The average rank score for the flexible printed circuit was determined to be 9.8 (Table 1).

Example 5

A flexible printed circuit was manufactured and combined with a dermally acceptable adhesive. A 25 micron thick non-porous urethane film (PT1710S, Deerfield Urethanes, Whately, Mass.) was obtained and used as the printing substrate.

Surface-Printing Conductive Traces onto a Substrate for Skin Contact

Surface printing of the conductive trace on the non-porous urethane substrate was conducted using the procedure described in Example 2.

Load Required to Double the Resistance Test

The flexible printed circuit was tested using the Load Required to Double the Resistance Test described in the Test Method section set forth above. The load applied to cause a 2× increase in resistance was determined to be 0.6875 Newtons (Table 1).

MTVR

The moisture vapor transmission rate was measured using the test method entitled "Moisture Vapor Transmission Rate (MVTR) Measurement for Skin Contact Samples" set forth herein. The MVTR was determined to be 875 g/m²/24 hours (Table 1).

Peak Compression Load Test

The peak load was measured as described in the test method entitled "Peak Compression Load Test (Compressive Buckling)" set forth above. The peak load was determined to be 0.04337 Newtons (Table 1).

Example 6

A flexible printed circuit was manufactured and combined with a dermally acceptable adhesive. An approximately 50.8 µm thick, clear polyethylene terephthalate (PET) film (Dura-Lar, McMaster-Carr 8567K22) was obtained and used as the printing substrate.

Surface-Printing Conductive Traces onto a Substrate for Skin Contact

Surface printing of the conductive trace on the PET film substrate was conducted using the procedure described in Example 2.

Load Required to Double the Resistance Test

The flexible printed circuit was tested using the Load Required to Double the Resistance Test described in the Test Method section set forth above. The load applied to cause a 2× increase in resistance was determined to be 82.65 Newtons (Table 1).

MTVR

The moisture vapor transmission rate was measured using the test method entitled "Moisture Vapor Transmission Rate (MVTR) Measurement for Skin Contact Samples" set forth herein. The MVTR was determined to be 130 g/m²/24 hours (Table 1).

Peak Compression Load Test

The peak load was measured as described in the test method entitled "Peak Compression Load Test (Compressive Buckling)" set forth above. The peak load was determined to be 19.7540 Newtons (Table 1).

Example 7

A flexible printed circuit was manufactured and combined with a dermally acceptable adhesive. An approximately 12.7 µm thick, clear polyethylene terephthalate (PET) film (Dura-Lar, McMaster-Carr 8567K104) was obtained and used as the printing substrate.

Surface-Printing Conductive Traces onto a Substrate for Skin Contact

Surface printing of the conductive trace on the PET film substrate was conducted using the procedure described in Example 2.

Load Required to Double the Resistance Test

The flexible printed circuit was tested using the Load Required to Double the Resistance Test described in the Test Method section set forth above. The load applied to cause a 2× increase in resistance was determined to be 20.9 Newtons (Table 1).

MTVR

The moisture vapor transmission rate was measured using the test method entitled "Moisture Vapor Transmission Rate (MVTR) Measurement for Skin Contact Samples" set forth herein. The MVTR was determined to be 80 g/m²/24 hours (Table 1).

Peak Compression Load Test

The peak load was measured as described in the test method entitled "Peak Compression Load Test (Compressive Buckling)" set forth above. The peak load was determined to be 0.9335 Newtons (Table 1).

On-Skin Comfort Test

On-skin comfort was determined utilizing the test method entitled "On-Skin Comfort Test" set forth above. The average rank score for the sample was determined to be 4.3 (Table 1).

Example 8

An ePTFE membrane made generally according to the teachings described in U.S. Pat. No. 3,953,566 to Gore was provided. The ePTFE membrane had a mass per area of about 19 g/m², a porosity of about 56%, a thickness of about 25 µm, a bubble point of about 159 KPa, a matrix tensile strength of about 48 MPa in the longitudinal direction, and a matrix tensile strength of about 97 MPa in the transverse direction.

Figure 8:
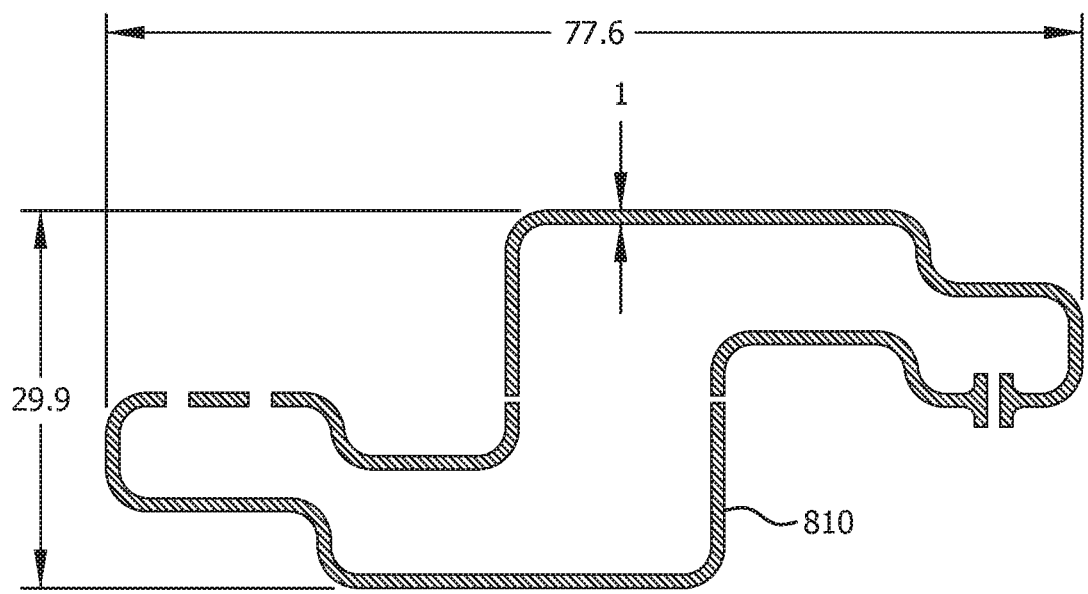
FIG. 8 is a schematic depiction of the printed pattern of electrically conductive ink printed on the ePTFE membrane in Example 8 according to at least one embodiment.

The ePTFE membrane was restrained in a 14 inch (~35.56 cm) diameter embroidery hoop and screen printed using conductive ink (CI1036; Engineered Conductive Materials, Delaware, Ohio) in the pattern shown in FIG. 8. The dimensions shown in FIG. 8 are in mm and are shown for to indicate the size and print of the pattern. The screen printing was performed using a model MSP-088 screen printer (HMI Manufacturing, Lebanon, N.J.), a stainless steel screen with 200 TPI, 1.6 mil wire diameter, and 12.7 µm emulsion of the electrically conducive ink. The ink was dried in a convection oven at 160° C. for 10 minutes. The electrically conductive trace on the ePTFE membrane is the flexible printed circuit.

Figure 9:
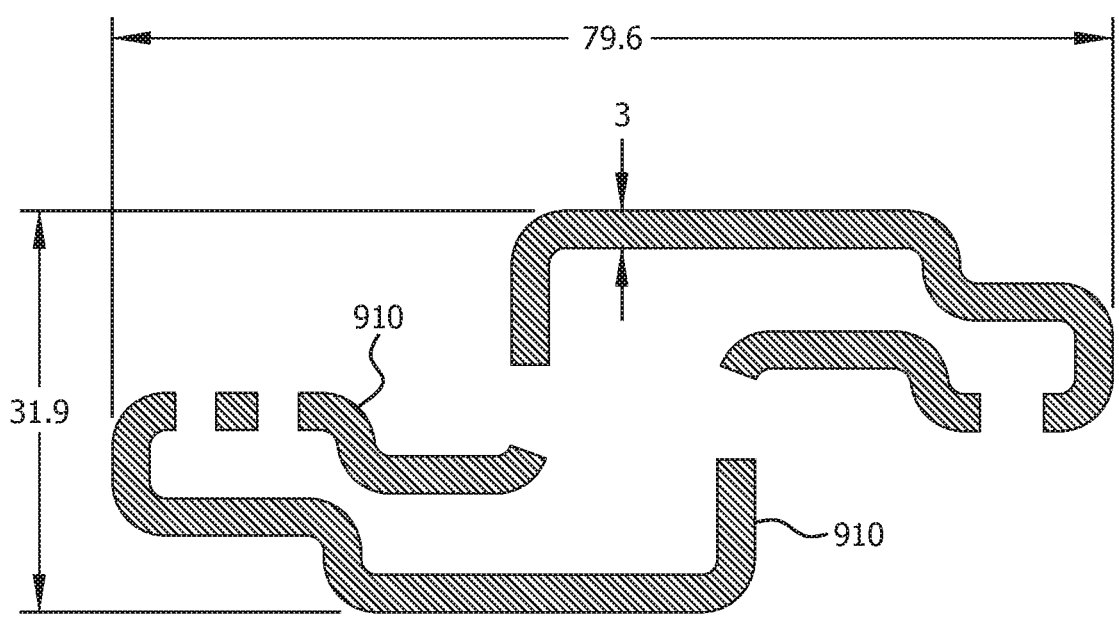
FIG. 9 is a schematic depiction of an insulative overcoat applied over the majority of the printed pattern shown in FIG. 8 and described in Example 8 according to at least one embodiment.

A dielectric overcoat 910 (ink, stretchable, ultraviolet light (UV)-cure insulator; DI-7540; Engineered Conductive Materials, Delaware, Ohio) was then applied over most of the previously printed conductive trace 810 in the pattern shown in FIG. 9. The dimensions shown in FIG. 9 are in mm and are shown to indicate the size and print of the pattern. The dielectric overcoat 910 was cured by exposing it to UV light for about 30 seconds using a PORTA-RAY® 400 (a portable UV light curing system; Dymax Corp., Torrington, Conn.).

Figure 10:
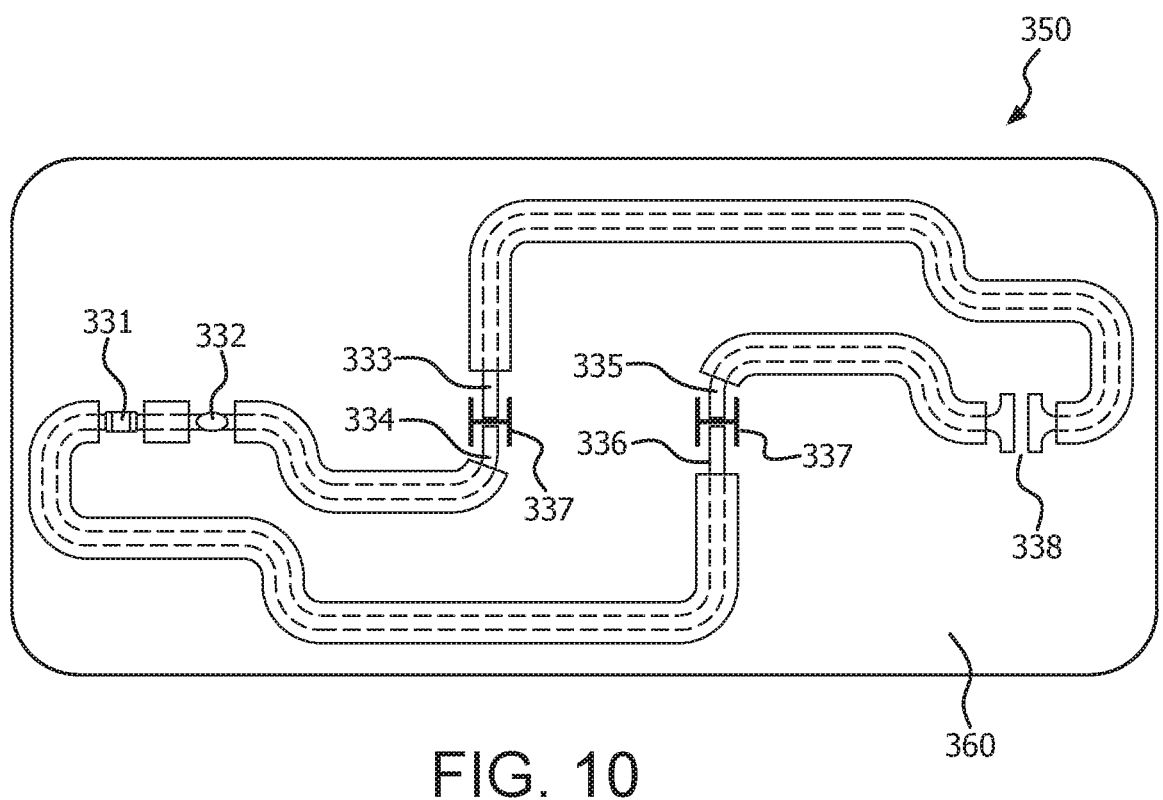
FIG. 10 is a schematic depiction of a printed circuit board having a surface mount light-emitting diode adhered to the ePTFE membrane using electrically conductive ink as described in Example 8 according to at least one embodiment.

A surface mount light-emitting diode (LED) 331 was adhered to the printed ePTFE membrane 360 using electrically conductive ink (CI1036 Engineered Conductive Materials, Delaware, Ohio) as shown in FIG. 10 to create a flexible printed circuit board. Additional ink was applied to make an electrical connection 332 as shown in FIG. 10. The conductive ink was dried in a convection oven at 130° C. for approximately 10 minutes. A UV-curable encapsulant (EC-9519; Engineered Conductive Materials, Delaware, Ohio) was applied over the LED 331 and electrical connection 332. The encapsulant was cured with 30 seconds of UV exposure in a 400 watt Dymax cure station (Dymax Corp.).

ARCARE® 7396 pressure sensitive adhesive (Adhesives Research, Glen Rock, Pa.) was then applied to the unprinted side of the ePTFE membrane. H-shaped cuts 337 were made in the ePTFE membrane 360 as shown in FIG. 10. The resulting flaps 333, 334, 335, and 336, each supported an exposed trace of conductive ink, were folded to the back of the ePTFE membrane 360. A 3 mm circle of ARCARE® 90366 conductive pressure sensitive adhesive (Adhesives Research, Glen Rock, Pa.) was applied to each flap 333, 334, 335, and 336.

Figure 11:
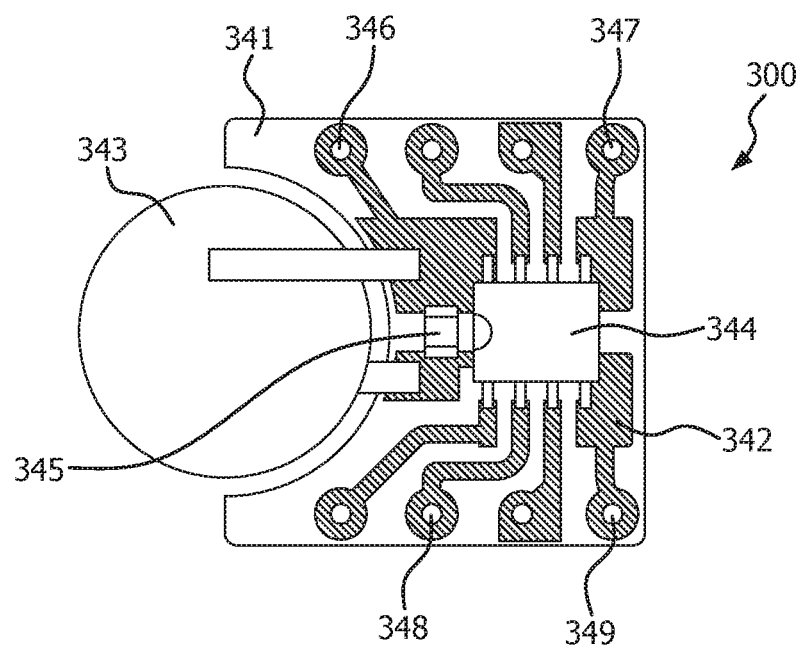
FIG. 11 is a schematic depiction of an electronic module having a lithium battery, processor, and a capacitor soldered to patterned copper traces as described in Example 8 according to at least one embodiment.
Figure 12:
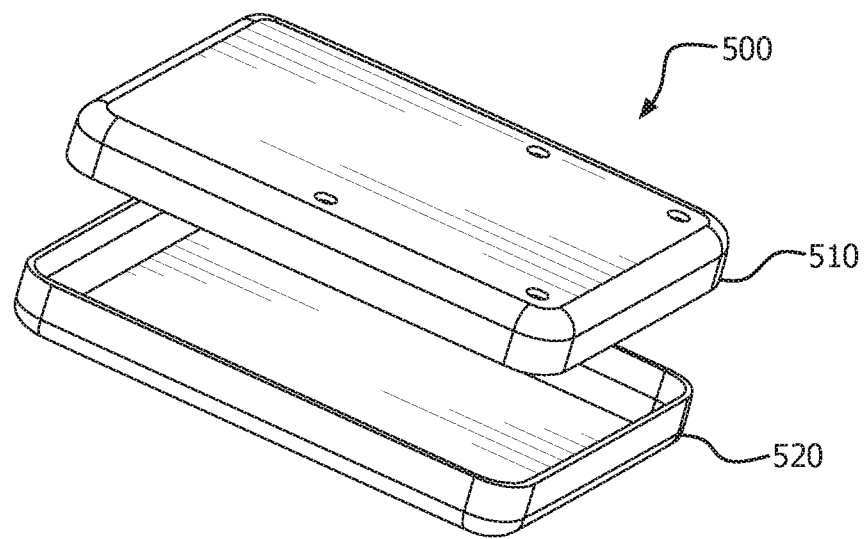
FIG. 12 shows a two part housing machined from polycarbonate with a wall thickness of about 0.3 mm and outside dimensions of about 25.2 mm×19.4 mm×4 mm as described in Example 8 according to at least one embodiment.

Next, an electronic module was prepared. An electronic module is defined herein as an assembly that includes more than two or more electronic components that are electrically coupled. A single-sided 1/16 inch thick copper clad FR4 PCB 341 (473-1000-ND, Digi-Key, Thief River Ralls, Minn.)

was machined in the outline and copper pattern 342 shown in FIG. 11. A battery 343 (3V lithium battery; coin shape, 12.5 mm; P663-ND, Digi-Key, Thief River Falls, Minn.), a processor 344 (Atmel 8-bit AVR Microcontroller; ATTINY85V-10SU-ND, Digi-Key, Thief River Falls, Minn.), and a 1 µF capacitor 345 (445-8890-1-ND, Digi-Key, Thief River Falls, Minn.) were soldered to the copper traces as shown in FIG. 11. Header pins were placed in through-holes in the board at locations 346, 347, 348, 349 so that the pins were nearly flush with the copper traces and protruded several mm through the board. A two-part housing 500 having a first half 510 and a second half 520 was machined from polycarbonate with a wall thickness of about 0.3 mm and outside dimensions of about 25.2 mm×19.4 mm×4 mm and is shown in FIG. 12. The flexible printed circuit board was glued into one half of the housing using epoxy adhesive (Locktite 79340-68620, Henkel Corp. Rocky Hill, Conn.) with the header pins extending through the housing.

Once the epoxy cured, the header pins were clipped and ground flush with the housing, creating electrical contacts. ECOFLEX™ 00-35 FAST Silicone (a soft, fast cure platinum-catalyzed silicone; Smooth-on, Macungie, Pa.) was poured into the housing and allowed to surround the circuit board. The second half 520 of the housing was assembled onto the first half 510 and held in place while the silicone cured. Electrically conductive ink (CI1036, Engineered Conductive Materials, Delaware, Ohio) was printed onto the housing and on top of the electrical contacts 365, 366, 367, 368 forming features 361, 362, 363, and 364 in the pattern shown in FIG. 13. The conductive ink was allowed to dry in an oven for 20 minutes at 60° C.

Figure 13:
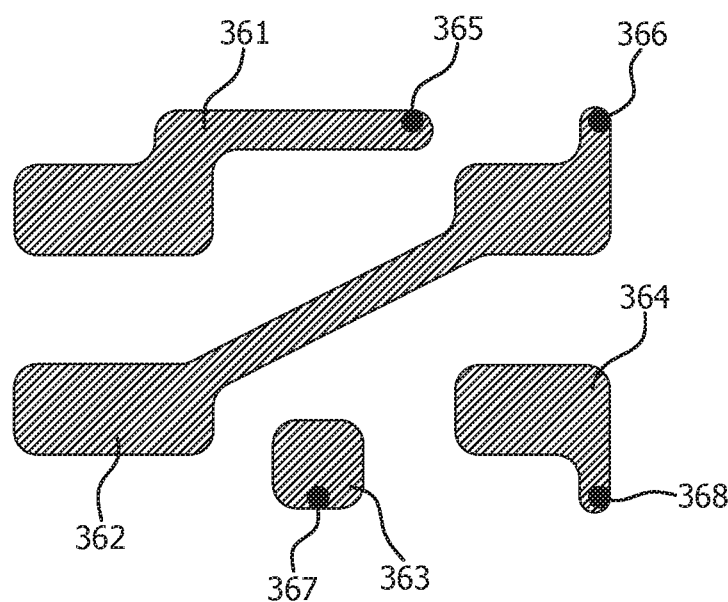
FIG. 13 is a schematic depiction of the conductive ink pattern printed on the housing depicted in FIG. 12 which was used to make the electronic module described in Example 8 according to at least one embodiment.

The electronic module 300 was attached to the flexible circuit 350 so that the flaps 333, 335, 334, and 336 in FIG. 10 were connected to the conductive ink portions 364, 362, 362, and 361 shown in FIG. 13, respectively. This created a hybrid flexible printed circuit board that included an electronic module and the flexible printed circuit board. The processor 334 in FIG. 11 was pre-programmed to flash the LED 331 5 times after the electrical contacts 338 were connected with an electrically conductive object. This demonstrated that the electronic module was able to communicate electrically with the hybrid flexible printed circuit board.

Figure 15:
FIG. 15 is an image of a flexible printed circuit placed onto the bend of an arm of a human subject when the arm is extended according to at least one embodiment.
Figure 16:
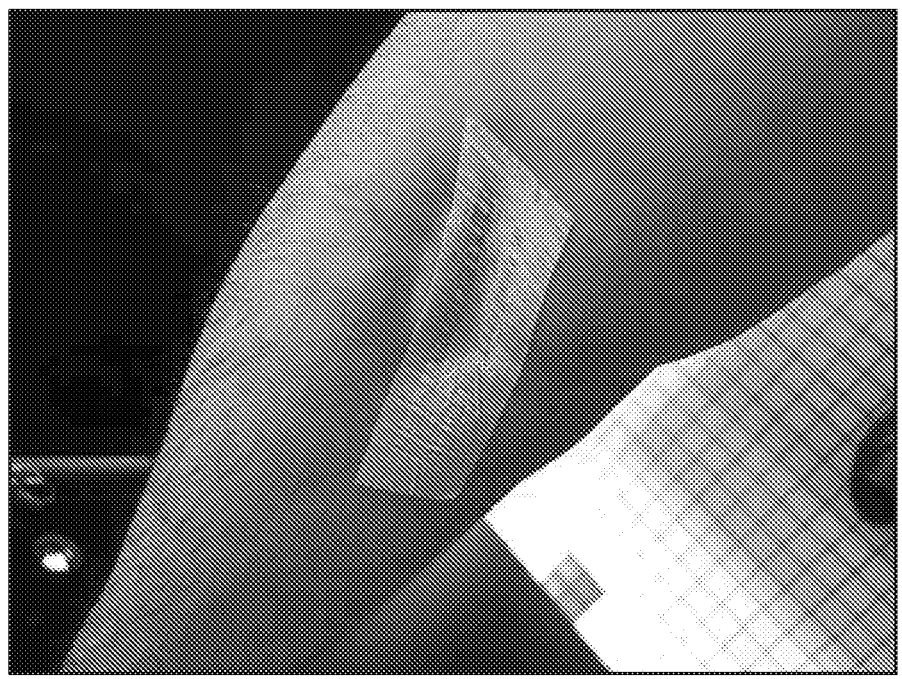
FIG. 16 is an image of the flexible circuit of FIG. 15 in a slightly bent configuration showing the conformation of the flexible printed circuit to the skin by compressing and wrinkling according to at least one embodiment.

The hybrid flexible printed circuit board was removed from the embroidery hoop by trimming the ePTFE membrane around the perimeter of the conductive ink, leaving an approximately 5-10 mm border. The hybrid flexible printed circuit board was attached to the forearm of a subject while the subject's arm was straight at the elbow and the subject's wrist was in full extension, as pictured in FIG. 15. Holding this position while attaching the hybrid flexible printed circuit board kept the subject's skin in tension. When the subject relaxed his elbow and wrist, the flexible circuit board easily conformed to the skin by compressing and wrinkling, as shown in FIG. 16. It was noted that after 5 days of wear, the hybrid flexible printed circuit board continued to function.

TABLE 1

Summary of Data

| Example | Printing Substrate | Conductive Ink Location | Load @ 2X Resistance (Newton) | Moisture Vapor Transmission Rate (g/m$^2$/24 hours) | Compressive Buckling Average Peak Load (newton) | On-Skin Comfort test Scale (1-10)[b] |
|---|---|---|---|---|---|---|
| 1 | ePTFE Type I | Imbibed | 1.490 | 593 | 0.05 | N.D.[a] |
| 2 | ePTFE Type I | Surface | 2.379 | 586 | 0.08 | N.D. |
| 3 | ePTFE Type 2 | Surface | 1.518 | 745 | 0.14 | 8.5 |
| 4 | PE membrane | Surface | 5.627 | 340 | 0.58 | 9.8 |
| 5 | Urethane (nonporous) | Surface | 0.688 | 875 | 0.04 | N.D. |
| 6 | PET 50.8 µm thickness | Surface | 82.665 | 130 | 19.75 | N.D. |
| 7 | PET 12.7 µm thickness | Surface | 20.900 | 80 | 0.93 | 4.3 |

[a] = Not determined (N.D.)
[b] = Scale from 1 (uncomfortable; most noticeable) to 10 (most comfortable; least noticeable)

What is claimed is:

1. A flexible printed circuit comprising:
   a microporous synthetic polymer membrane having a node and fibril microstructure; said microporous synthetic polymer membrane having a first surface and a second surface; and
   at least one electrically conductive trace, said at least one electrically conductive trace disposed directly on at least one of said first surface and said second surface; and
   a dermally acceptable adhesive positioned on at least one of said first surface and said second surface of said microporous synthetic polymer membrane.

2. The flexible printed circuit of claim 1, wherein said at least one electrically conductive trace is positioned on said first surface and said dermally acceptable adhesive is positioned on said second surface.

3. The flexible printed circuit of claim 1, wherein said at least one electrically conductive trace is positioned on said first surface and said second surface and said dermally acceptable adhesive is positioned on at least one of said first surface and said second surface.

4. The flexible printed circuit of claim 3, further comprising an imbibed electrically conductive trace electrically interconnecting said at least one electrically conductive trace on said first surface with said at least one electrically conductive trace on said second surface.

5. The flexible printed circuit of claim 1, wherein the microporous synthetic polymer membrane is selected from expanded polytetrafluoroethylene (ePTFE), poly (p-xylylene) (ePPX), porous ultra-high molecular weight polyethylene (eUHMWPE), porous ethylene tetrafluoroethylene (eETFE) and porous polylactic acid (ePLLA).

6. The flexible printed circuit of claim 1, wherein the microporous synthetic polymer membrane is a microporous expanded fluoropolymer.

7. The flexible printed circuit of claim 1, wherein the microporous synthetic polymer membrane is an expanded polytetrafluoroethylene membrane.

8. The flexible printed circuit of claim 1, wherein the at least one electrically conductive trace is selected from electrically conductive metal nanoparticles, nanoparticles of electrically conductive materials, electrically conductive nanotubes, electrically conductive metal particles, electrically conductive polymers and combinations thereof.

9. The flexible printed circuit of claim 1, wherein the at least one electrically conductive trace comprises particles or nanoparticles of silver, platinum, gold, copper, carbon black, graphite and combinations thereof.

10. The flexible printed circuit of claim 1, wherein the at least one electrically conductive trace comprises a continuous network of conductive nanoparticles.

11. The flexible printed circuit of claim 1, wherein the at least one electrically conductive trace has a form of an electrically conductive pattern or a circuit.

12. The flexible printed circuit of claim 1, wherein the flexible printed circuit has a flexibility of less than about 1.0 newton as evidenced by the Peak Compression Load Test (Compressive Buckling) test method.

13. The flexible printed circuit of claim 1, wherein a load applied to cause a 2X increase in resistance is greater than about 0.7 newtons when tested according to the Load Required to Double the Resistance test method.

14. The flexible printed circuit of claim 1, further comprising an insulative overcoat positioned over at least a portion of said at least one electrically conductive trace.

15. The flexible printed circuit of claim 1, comprising at least one electric component.

16. The flexible printed circuit of claim 15, wherein the at least one electric component is selected from electron resistors, capacitors, light emitting diodes (LEDs), integrated circuits, sensors, power sources, data transmitters, data receivers and combinations thereof.

17. The flexible printed circuit of claim 1 comprising an electronic module and, optionally at least one electric component.

18. The flexible printed circuit of claim 17, wherein said electronic module is positioned on a same side of the microporous synthetic polymer membrane as the at least one electrically conductive trace.

19. The flexible printed circuit of claim 17, wherein said electronic module is configured to be positioned between said microporous synthetic polymer membrane and a skin of a user.

20. A flexible printed circuit comprising:
a microporous synthetic polymer membrane having a node and fibril microstructure;
at least one electrically conductive trace, said at least one electrically conductive trace being imbibed within said microporous synthetic polymer membrane; and
a dermally acceptable adhesive positioned on said microporous synthetic polymer membrane.

21. The flexible printed circuit of claim 20, wherein the microporous synthetic polymer membrane is selected from expanded polytetrafluoroethylene (ePTFE), poly (p-xylylene) (ePPX), porous ultra-high molecular weight polyethylene (eUHMWPE), porous ethylene tetrafluoroethylene (eETFE) and porous polylactic acid (ePLLA).

22. The flexible printed circuit of claim 20, wherein the microporous synthetic polymer membrane is an expanded fluoropolymer membrane.

23. The flexible printed circuit of claim 20, wherein the microporous synthetic polymer membrane is an expanded polytetrafluoroethylene membrane.

24. The flexible printed circuit of claim 20, wherein the at least one electrically conductive trace fills pores of the microporous synthetic polymer membrane through a thickness thereof.

25. The flexible printed circuit of claim 20, wherein the at least one electrically conductive trace is selected from electrically conductive metal particles, electrically conductive metal nanoparticles, nanoparticles of electrically conductive materials, electrically conductive nanotubes, electrically conductive metal flakes, electrically conductive polymers and combinations thereof.

26. The flexible printed circuit of claim 20, wherein the at least one electrically conductive trace comprises particles or nanoparticles of silver, platinum, gold, copper, carbon black, graphite and combinations thereof.

27. The flexible printed circuit of claim 20, wherein the at least one electrically conductive trace comprises a continuous network of conductive particles.

28. The flexible printed circuit of claim 20, wherein the at least one electrically conductive trace has a form of an electrically conductive pattern or a circuit.

29. The flexible printed circuit of claim 20, wherein the flexible printed circuit has a flexibility of less than about 1.0 newton as evidenced by the Peak Compression Load Test (Compressive Buckling) test method.

30. The flexible printed circuit of claim 20, wherein a load applied to cause a 2X increase in resistance is greater than about 0.7 newtons when tested according to the Load Required to Double the Resistance test method.

31. The flexible printed circuit of claim 20, comprising an insulative overcoat positioned over at least a portion of said at least one electrically conductive trace.

32. The flexible printed circuit of claim 20, comprising at least one electric component.

33. The flexible printed circuit of claim 32, wherein the at least one electric component is selected from electron resistors, capacitors, light emitting diodes (LEDs), integrated circuits, sensors, power sources, data transmitters, data receivers and combinations thereof.

34. The flexible printed circuit of claim 20, comprising an electronic module.

35. The flexible printed circuit of claim 34, wherein said electronic module is positioned on a same side of the microporous synthetic polymer membrane as the at least one electrically conductive trace.

36. The flexible printed circuit of claim 34, wherein said electronic module is configured to be positioned between said microporous synthetic polymer membrane and a skin of a user.

37. A hybrid flexible printed circuit board comprising:
an expanded polytetrafluoroethylene (ePTFE) membrane having a node and fibril microstructure,
wherein said ePTFE membrane contains at least one trace of conductive nanoparticles on a surface thereof;
a dermally acceptable adhesive positioned on said ePTFE membrane on a side opposing said at least one trace of conductive nanoparticles, and an electronic module electrically coupled to said at least one trace of conductive nanoparticles.

38. A hybrid flexible printed circuit board comprising:
an expanded polytetrafluoroethylene membrane having a node and fibril microstructure,
  wherein said expanded polytetrafluoroethylene membrane has a first side and a second side; and
at least one electrically conductive trace, said at least one electrically conductive trace being located directly on at least one of said first side and said second side of said expanded polytetrafluoroethylene membrane;
a dermally acceptable adhesive positioned on at least one side of said expanded polytetrafluoroethylene membrane; and
an electronic module electrically coupled to said at least one electrically conductive trace.

39. A flexible printed circuit comprising:
an expanded polytetrafluoroethylene membrane having a node and fibril microstructure;
at least one electrically conductive trace, said at least one electrically conductive trace being imbibed within said expanded polytetrafluoroethylene membrane;
a dermally acceptable adhesive positioned on said expanded polytetrafluoroethylene membrane on a side opposing said at least one electrically conductive trace; and
an electronic module electrically coupled to said at least one electrically conductive trace.

40. An article comprising the flexible printed circuit of claim 1.

41. An article comprising the flexible printed circuit of claim 20.

42. An article comprising the flexible printed circuit of claim 17.

43. An article comprising the flexible printed circuit of claim 34.

44. An article comprising the flexible printed circuit of claim 15.

45. An article comprising the flexible printed circuit of claim 32.

* * * * *